United States Patent [19]

Bolhofer et al.

[11] 4,203,988
[45] May 20, 1980

[54] PYRIDINYL UREAS AND PHARMACEUTICAL USE

[75] Inventors: William A. Bolhofer, Frederick; Edward J. Cragoe, Jr., Lansdale; Jacob M. Hoffman, Jr., North Wales, all of Pa.

[73] Assignee: Merck & Co., Inc., Rahway, N.J.

[21] Appl. No.: 943,581

[22] Filed: Sep. 18, 1978

Related U.S. Application Data

[63] Continuation-in-part of Ser. No. 727,907, Sep. 29, 1976, abandoned, which is a continuation-in-part of Ser. No. 631,300, Nov. 12, 1975, abandoned.

[51] Int. Cl.$^2$ .................... A61K 31/44; C07D 213/75
[52] U.S. Cl. .................... 424/266; 424/246; 424/248.5; 424/248.52; 424/248.53; 424/248.54; 424/248.55; 424/250; 424/258; 424/263; 424/267; 544/58.6; 544/131; 544/360; 546/162; 546/193; 546/281; 546/287; 546/288; 546/289; 546/292; 546/305; 546/306
[58] Field of Search ................ 424/263, 266; 546/305, 546/306, 292, 287, 288, 289

[56] References Cited

U.S. PATENT DOCUMENTS

| | | | |
|---|---|---|---|
| 2,042,023 | 5/1936 | Schonhofer et al. | 546/171 |
| 2,639,285 | 5/1953 | Sondern et al. | 260/306.8 R |
| 3,404,152 | 10/1968 | Thiele et al. | 546/306 |
| 3,864,496 | 2/1975 | Diamond et al. | 424/326 |
| 3,894,151 | 7/1975 | Black et al. | 424/246 |
| 3,896,233 | 7/1975 | Brenner et al. | 424/248 |
| 3,897,555 | 7/1975 | Loev | 424/263 |
| 3,920,822 | 11/1975 | Durant et al. | 424/263 |

FOREIGN PATENT DOCUMENTS

| | | |
|---|---|---|
| 819436 | 2/1975 | Belgium. |
| 834247 | 2/1976 | Belgium. |
| 1267433 | 3/1972 | United Kingdom. |

OTHER PUBLICATIONS

Burger, Medicinal Chemistry, 2nd Edition (1960), p. 497.
Burger, Medicinal Chemistry, 3rd Edition (1970), p. 1588.

*Primary Examiner*—Richard Raymond
*Attorney, Agent, or Firm*—David L. Rose; Harry E. Westlake

[57] ABSTRACT

Compounds of the formula

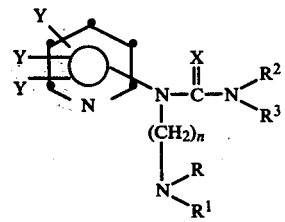

have been found to inhibit gastric secretion in mammalian species.

30 Claims, No Drawings

PYRIDINYL UREAS AND PHARMACEUTICAL USE

CROSS REFERENCE TO RELATED APPLICATIONS

This application is a continuation-in-part of application Ser. No. 727,907, filed Sept. 29, 1976, now abandoned, which is a continuation-in-part of application Ser. No. 631,300, filed Nov. 12, 1975, now abandoned.

BACKGROUND OF THE INVENTION

Excess secretion of gastric acid can cause indigestion and stomach distress and, if prolonged, can result in ulcer formation. Treatment of excess secretion of gastric acid has heretofore consisted mainly of a bland diet, abstinence from certain foods and the use of antacids to neutralize the gastric acid after it was secreted into the stomach. An improved method of treatment would be to inhibit gastric acid secretion.

OBJECTS OF THE INVENTION

It is an object of the present invention to provide compounds which inhibit gastric secretion. Another object is to provide methods for the preparation of these compounds. A further object is to provide pharmaceutical formulations for the administration of these compounds. Still another object is to provide a method of inhibit gastric secretion. These and other objects of the present invention will become apparent from the following description.

SUMMARY OF THE INVENTION

Compounds of the formula

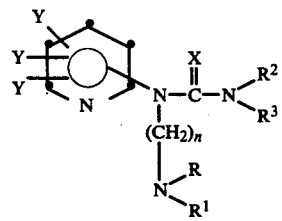

wherein n is 2–8 and 1–4 hydrogen in the alkylene chain may be replaced by lower alkyl; R, $R^1$, $R^2$ and $R^3$ are H, lower alkyl, aralkyl, cycloalkyl, cycloalkylmethyl, hydroxyalkyl, alkoxyalkyl, alkylcarbonyloxyalkyl, haloalkyl, phenyl, substituted phenyl or

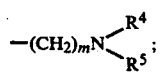

or 2 of the R-substituents attached to the same nitrogen atom may be joined to form a 5- or 6-membered ring which may contain up to 2 additional heteroatoms; the Y substituents may be the same or different and are H, lower alkyl, hydroxyalkyl, deuteroalkyl, phenyl, hydroxy, halogen,

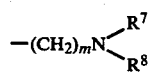

haloalkyl, alkoxy, aralkoxy, alkylthio, alkylsulfonyl, cyano or nitro, formyl, alkoxycarbonyl, carbamoyl, morpholino or piperidino;

or adjacent Y-substituents on the pyridine ring may form a benzene ring;

and X is oxygen or sulfur;

and the quaternary ammonium or N-oxide derivatives thereof and the pharmaceutically acceptable acid-addition salts thereof have been found to inhibit gastric secretion.

DETAILED DESCRIPTION

The present invention is directed to compounds of the formula

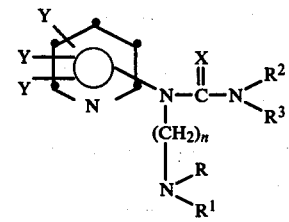

wherein n is a whole number from 2 to 8 and up to 4 hydrogen atoms in the alkylene chain $(CH_2)_n$ may be replaced by alkyl of 1–3 carbon atoms;

R, $R^1$, $R^2$ and $R^3$ are hydrogen or alkyl of from 1 to 8 carbon atoms; aralkyl; cycloalkyl of from 3 to 7 carbon atoms in the ring; cycloalkylmethyl with from 3 to 7 carbon atoms in the ring, alkoxyalkyl wherein alkoxy is 1–4 carbon atoms and alkyl is 1–4 carbon atoms; lower alkylcarbonyloxyalkyl; hydroxyalkyl of from 1 to 4 carbon atoms; haloalkyl of 1 to 3 carbon atoms;

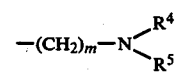

wherein m is 0, 2 or 3 and $R^4$ and $R^5$ are the same or different and are hydrogen or alkyl of from 1 to 4 carbon atoms; phenyl; substituted phenyl wherein the substituent is alkyl of from 1 to 3 carbon atoms, alkoxy of from 1 to 3 carbon atoms, halogen (F, Cl, Br or I) or haloalkyl of from 1 to 3 carbons wherein the halogen is F, Cl, Br or I; or 2 of the R-substitutents attached to the same nitrogen atom are joined to form a 5- or 6-membered ring (with loss of a total of two hydrogen atoms) which may contain up to two additional heteroatoms selected from O, S, or N-$R^6$ wherein $R^6$ is hydrogen, alkyl of from 1 to 4 carbons or aralkyl;

the Y substituents may be the same or different and are hydrogen, alkyl of from 1 to 4 carbon atoms; hydroxyalkyl of 1 to 4 carbon atoms, deuteroalkyl of 1 to 4 carbon atoms, phenyl, hydroxy, halogen (F, Cl, Br

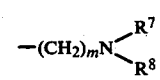

wherein m is 0, 1, 2, or 3 and $R^7$ and $R^8$ are the same or different and are hydrogen, alkyl of from 1 to 4 carbon atoms or aralkyl, haloalkyl and polyhaloalkyl of from 1 to 4 carbon atoms, alkoxy of from 1 to 4 carbon atoms, aralkoxy, alkylthio of from 1 to 4 carbon atoms, alkylsulfonyl of 1 to 4 carbon atoms, cyano, nitro, formyl, lower alkoxycarbonyl wherein alkoxy is 1 to 5 carbon atoms, carbamoyl; morpholino or piperidino;

or the 2 Y-substituents on adjacent carbon atoms of the pyridine ring are joined to form a benzene ring which together with the pyridyl nucleus forms a quinoline ring system;

and X is oxygen or sulfur;

and the quaternary ammonium or N-oxide derivatives thereof, and the pharmaceutically acceptable acid-addition salts thereof.

The aralkyl group may be, for example, benzyl or phenethyl and the cycloalkyl group may be, for example, cyclopropyl, cyclobutyl, cyclopentyl, cyclohexyl or cycloheptyl.

Examples of some 5- or 6-membered rings formed by joining 2 R groups attached to the same nitrogen atom are for instance, pyrrolidino, piperidino, alkylpiperidino, wherein the alkyl group is from 1 to 4 carbon atoms, morpholino, thiomorpholino, piperazino, 4-alkylpiperazino, wherein the alkyl group is from 1 to 4 carbon atoms, or 4-benzylpiperazino.

Preferred compounds of the present invention are encompassed by the general formula

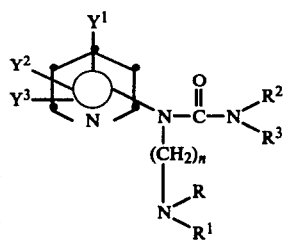

wherein n, R, $R^1$, $R^2$ and $R^3$ have the meaning given above, $Y^1$ is hydrogen, alkyl of from 1 to 4 carbon atoms alkoxy of 1 to 4 carbon atoms, haloalkyl of 1 to 3 carbon atoms, hydroxyalkyl of 1 to 4 carbon atoms, deuteroalkyl of 1 to 4 carbon atoms or alkylthio of 1 to 4 carbon atoms, $Y^2$ is hydrogen, alkyl of 1–4 carbon atoms or halogen, and $Y^3$ is hydrogen, alkyl of from 1 to 4 carbon atoms, haloalkyl of 1 to 3 carbon atoms, hydroxyalkyl of 1 to 4 carbon atoms, deuteroalkyl of 1 to 4 carbon atoms, amino, alkylamino of from 1 to 4 carbon atoms, diloweralkylamino wherein each alkyl may have from 1 to 4 carbon atoms or halogen. The compounds of the present invention have been found to inhibit gastric secretion in mammalian species, e.g., dogs, at a dose level of from about 5 about 200 mg/kg.

Unless indicated otherwise, all temperatures throughout this disclosure are expressed in degrees Celsius.

The compounds of the present invention may be prepared by reacting a 2-aminopyridine, II (wherein the amino group is substituted by a labile activating group Z) with an $R,R^1$-amino-alkyl halide III wherein q is 2 or 3 and wherein the halide preferably is chlorine, to form the corresponding N-(Z-group)-N-(R,$R1^1$-aminoalkyl)-N-(substituted 2-pyridyl)amine IV wherein n is 2 or 3 in the presence of a strong base such as sodium hydride, butyl lithium or lithium diisopropylamide in an appropriate solvent such as dimethylformamide, toluene, or dioxane and at reaction temperatures of from about −70° to about 160°, preferably from about 0° to about 100° C.

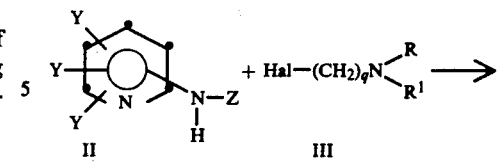

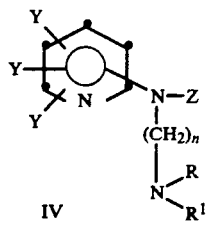

Removal of the labile activating group Z of the compound of formula IV hydrolytically under either acidic (aqueous mineral acid) a basic (alkali hydroxide) reaction conditions yields the compound IV A similar to IV except that Z is replaced by hydrogen. The compound of formula IV A is then reacted with an $R^2R^3$-carbamoyl halide or an $R^2R^3$-thiocarbamoyl halide V in the presence of an organic or inorganic base such as triethylamine or sodium carbonate and an inert solvent such as benzene at reaction temperatures of from about 20° to about 120°, preferably to about 75° to about 100° to form an N,N-($R^2$,$R^3$)-N'-(R-$R^1$-aminoalkyl)-N'-(substituted-2-pyridyl)urea or the corresponding thiourea, I.

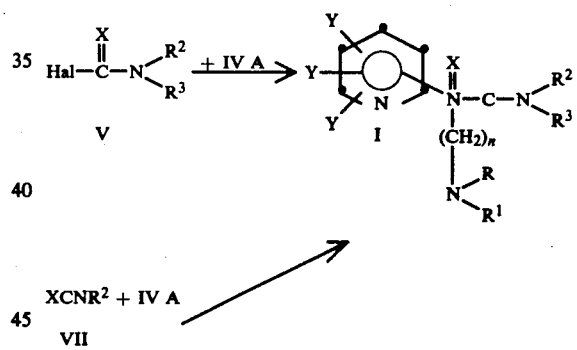

Alternatively, the compound of formula IV A is reacted with an isocyanate or isothiocyanate $XCNR^2$ of formula VII in an inert solvent such as benzene at temperatures of from about 20° to about 120°, preferably from about 20° to about 80° to form a compound of formula I wherein $R^3$ is H.

A compound of formula IV A wherein n is 4–6 is prepared by reacting a compound of formula II with a compound of the formula Br(CH$_2$)$_p$Cl, wherein p is 4–6 under conditions identical to that earlier described for the reaction of II with III to form a compound of the formula

IX and reacting the latter with an amine of the formula

in a polar solvent such as ethanol at reaction temperatures of from about 50° to about 150° preferably from about 90°- to about 120° advantageously in the presence of a catalyst such as cuprous chloride to yield a compound of formula IV wherein n is 4–6 which is converted to the corresponding compound of formula IV A wherein n is 4–6 as previously described.

The activating labile group Z may be any group readily bonded to the amino group of a compound of formula VI and which selectively can be removed therefrom as appropriate for succeeding reactions. Examples of such groups are acyl, e.g., acetyl, trifluoroacetyl, or formyl, or carbamoyl, e.g. N,N-dimethylcarbamoyl.

Alternatively, a compound of the formula IVA wherein n is 2–6 is prepared by reacting a compound of the formula

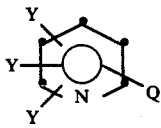

with a diamine of the formula

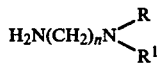

wherein Q is a group readily displaceable by the foregoing diamine, e.g., Q is halo, nitro, methylsulfonyl, or trimethylsilyl; in a solvent such as toluene, xylene, pyridine or an excess of the diamine itself at reaction temperatures of 50° to about 175°, preferably from about 100° to 150°.

An alternative process for the preparation of a compound of formula I wherein n is 2 or 3 and wherein X is oxygen is to react a 2-aminopyridine, VI, with a compound of formula V wherein X is oxygen in the presence of a strong base (i.e. sodium hydride or lithium hydride) in an inert solvent such as toluene, dioxane, tetrahydrofuran at reaction temperatures of from about 40° to about 120°, preferably from about 50° to about 100° to form a compound of formula VIII and reacting the latter with a compound of formula III to yield a compound of formula I under conditions similar to that described for the process wherein a compound of formula IV is prepared by reacting a compound of formula II with a compound of formula III.

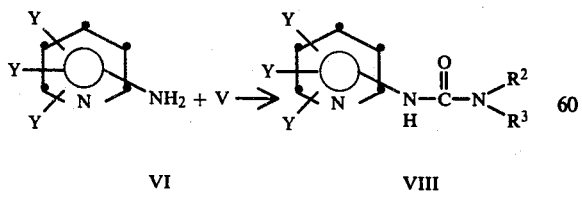

An alternative process for the preparation of a compound of formula I wherein n is 4–6 and wherein X is oxygen is to react a 2-aminopyridine VI with a compound of formula V wherein X is oxygen in the presence of a strong base (i.e. sodium hydride or lithium hydride) in an inert solvent such as toluene, dioxane, or tetrahydrofuran at a reaction temperature of from about 40° to about 120°, preferably at from about 50° to about 100°, to form a compound of formula VIII and reacting the latter with a compound of the formula $Br(CH_2)_p Cl$ wherein p is 4–6 under conditions similar to that described for the process wherein the compound of formula IV is prepared by reacting a compound of formula II with a compound of formula III, to yield a compound of the formula

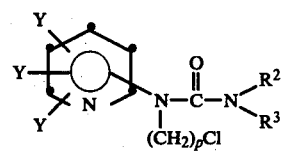

and reacting the latter with an amine of the formula

in a polar solvent such as ethanol at reaction temperatures from about 50° to about 150°, preferably from about 90° to about 120°, advantageously in the presence of a catalyst such as aqueous chloride to yield a compound of formula I wherein n is 4–6.

A compound of formula I wherein n is 2–6, X is 0 and $R^2$ and $R^3$ are preferably hydrogen is prepared by reacting a compound of formula IVA with cyanogen bromide in an inert solvent such as tetrahydrofuran at about 0°, preferably at about 50° or up to about 100°, and hydrolyzing the cyano product XI with an aqueous mineral acid such as hydrochloric at ambient temperature.

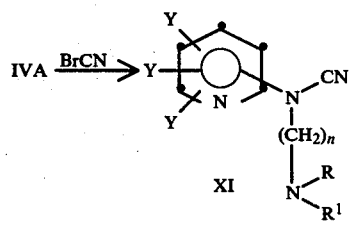

A method for the preparation of compounds of formula I in which R and $R^1$ are H, X is O or S and n is two involves the catalytic reduction of the nitrile XII in a suitable solvent such as ethyl acetate at elevated hydrogen pressures, e.g., up to about 200 psi, but usually at 50 psi in the presence of a noble metal catalyst such as platinum.

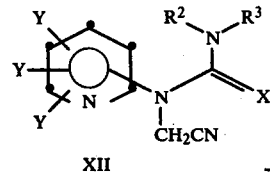

Compound II may be used as starting material to prepare Compound I using in place of Compound III, a Compound III A of the formula

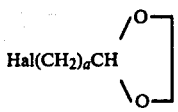

(III A)

wherein Hal is a halogen and a is a number of from 1 to 7. Following the described procedures there is obtained a compound of the formula

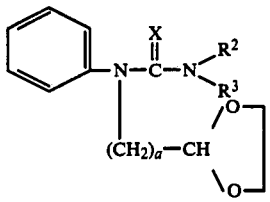

(XIII)

wherein X, n, R² and R³ are as above defined.

Compound XIII is treated with dilute aqueous mineral acid at room temperature for from 1 to 12 hours to prepare the aldehyde (Compound XIV)

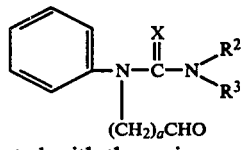

(XIV)

which is reacted with the amine,

in a polar solvent such as a lower alkanol, preferably methanol, at from 0° to 70° C., preferably room temperature, for ½ to 12 hours in the presence of excess sodium cyano borohydride to form Compound I. Additional stirring time, up to several days may be employed for slow reactions. Since the terminal formylcarbon atom is incorporated into the chain, the n-term of formula I is equivalent to a +1 in formula III A, XIII and XIV.

An alternative process for the preparation of compound IV A involves the following reaction scheme:

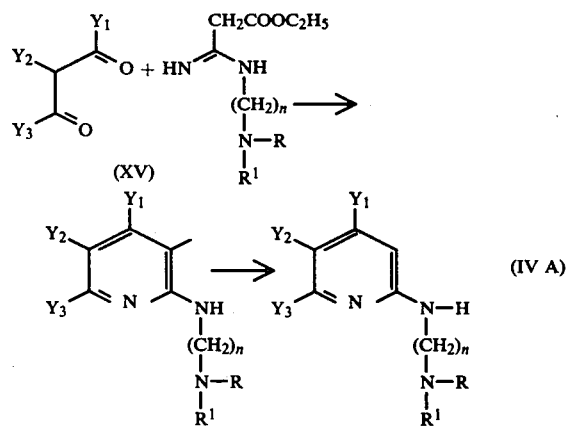

(XV)

(IV A)

The starting materials are combined in an aprotic solvent such as benzene, toluene and the like, and refluxed for 2 to 12 hours. Compound XV is hydrolized using known acidic or basic hydrolysis conditions to prepare Compound IV A. In the above formula, $Y_1$, $Y_2$ and $Y_3$ may be independently alkyl, deuteroalkyl, haloalkyl, and protected hydroxyalkyl where the protecting group is benzyl.

It will be apparent to those skilled in the art from the foregoing description and the following examples that certain products of formula I may in turn be converted to the end products of formula I. Specific instances of this type of transformation are set forth in Examples 49, 54, 66, 68, 71, 73 and 74.

The compounds of formula I of their quaternary ammonium or N-oxide derivatives may be used per se or in the form of their pharmaceutically acceptable acid-addition salts. The quaternary ammonium salts may be formed by reacting a compound of formula I wherein X is oxygen with alkyl halides (e.g., methyl iodide, isobutyl bromide, or dodecyl chloride) benzyl halides (e.g. benzyl bromides) or lowerdialkyl sulfates (e.g., dimethyl sulfate).

The N-oxide derivatives may be prepared by treating a compound of formula I wherein X is oxygen with hydrogen peroxide or a peroxycarboxylic acid such as m-chloroperoxybenzoic acid, peroxybenzoic acid or mono-peroxyphthalic acid.

The compound where Y is formyl are prepared from the analogous hydroxymethyl compound by oxidation. The preferred oxidizing agent is manganese dioxide suspended in an aprotic solvent such as chloroform or methylene chloride. The reaction is generally complete in from 12 to 60 hours at reflux. The product is isolated using known techniques.

From the formyl compound may be prepared the analogous difluoromethyl compound using diethylaminosulfur trifluoride. The reaction is carried out in an aprotic solvent, such as benzene, at reflux temperature and is generally complete in from 1 to 10 hours.

The deuteroalkyl compound are prepared from the compound of formula I where the Y groups are one or more alkyl groups. The starting material is reacted with perdeuterodimethylsulfoxide used in excess without any additional solvent, containing a catalytic amount of potassium tert-butoxide. The reaction mixture is heated preferably at about 0° C. for 10 to 24 hours. The progress of the reaction is conveniently following using nuclear magnetic resonance. The deutero compounds may also be prepared using the above described procedures and the appropriate deuterated starting materials since the deuterium atoms are not effected by such processes.

The compound of formula I forms acid addition salts by reaction with various inorganic and organic acids. The pharmaceutically acceptable acid-addition salts are prepared in known manner from, inter alia, inorganic acids, such as the hydrohalide acids (e.g., hydrochloric and hydrobromic acid), sulfuric acid, nitric acid, and phosphoric acid, and organic acids, such as maleic, fumaric, tartaric, citric, acetic, benzoic, 2-acetoxybenzoic, salicylic, succinic, p-aminobenzoic, p-acetamidobenzoic, or methanesulfonic acid and isethionic acid.

The compounds of the present invention in the described dosages may be administered orally, however, other routes such as intraperitoneal, subcutaneous, intramuscular or intravenous may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples illustrate the present invention without, however, limiting the same thereto. Unless indicated otherwise, all temperatures are expressed in degrees Celsius.

EXAMPLES 1–10

I.

N-(2-Dimethylaminoethyl)-N-(4,6-dimethyl-2-pyridyl)-N'-hexyl urea Hydrochloride

A.

N-(2-Dimethylaminoethyl)-N-(4,6-dimethyl-2-pyridyl)acetamide

One hundred and seventy seven grams (1.08 moles) of N-(4,6-dimethyl-2-pyridyl)acetamide is dissolved in 1.8 l of dry dimethylformamide in a 3 liter 3-neck flask equipped with a mechanical stirrer, thermometer, drying tube and slow nitrogen sweep. Sodium hydride in mineral oil (57%, 45.5 g) is added over a 30 minute period. After stirring for an additional 15 minutes, one hundred thirteen grams of 2-dimethylaminoethyl chloride hydrochloride is added in three portions over a 30 minute period. This is followed by 25.7 g of sodium hydride added in portions over a 60 minute period. Then 58.7 g of 2-dimethylaminoethyl chloride hydrochloride is added over a few minute period followed by 25.7 g of sodium hydride. A total of 96.9 g (2.3 mole) of 57% sodium hydride in mineral oil and 171.7 g (1.2 mole) of 2-dimethylaminoethyl chloride hydrochloride are used. The reaction mixture is stirred at 50° for 30 minutes then heated at 95° for 2½ hours. After adding 75 ml of ethanol and 75 ml of water, the dimethylformamide is removed by distillation in vacuum.

The residue is dissolved in dilute hydrochloric acid and the solution extracted three times with toluene. Then the aqueous phase is made alkaline (pH about 10) with sodium hydroxide and the mixture is extracted four times with methylene chloride. The combined methylene chloride extracts are extracted three times with water, once with saturated sodium chloride solution and then dried ($MgSO_4$). After removal of solvent, the residue is distilled to give 161.5 g product boiling at 140°–145°/1.25 mm.

B.

2-(2-Dimethylaminoethylamino)-4,6-dimethylpyridine

The product from part A is dissolved in a mixture of 500 ml ethanol and 500 ml 5 N sodium hydroxide and the solution is heated at reflux for 4 hours. Then the solution is acidified with concentrated hydrochloric acid and the solvents removed in vacuum. The residue is dissolved in 1 liter boiling isopropanol and the solution filtered to remove sodium chloride. The precipitate is washed four times with hot isopropanol. The combined filtrates are cooled to room temperature. The product is collected by filtration, washed with isopropanol and air dried to give 150.7 g of 2-(2-dimethylaminoethyl)-4,6-dimethylpyridine hydrochloride melting at 239°–241°. The hydrochloride salt is dissolved in water, made alkaline with sodium hydroxide (ph 10) and extracted with ether. The ether extract is washed with water (2X), saturated sodium chloride solution (1X), and then dried over magnesium sulfate. The solvent is removed in vacuum to give 116.9 g (56% yield) of 2-dimethylaminoethylamino-4,6-dimethylpyridine as a light yellow oil. This product distills at 138°–139°/2.1 mm.

C.

N-(2-Dimethylaminoethyl)-N-(4,6-dimethyl-2-pyridyl)N'-hexyl-urea Hydrochloride

A solution of 5.80 g (30.0 mmoles) of 2-(2-dimethylaminoethylamino)-4,6-dimethylpyridine in 50 ml of benzene is dried by azeotropic distillation. The solution is then treated with 7.63 g (60.0 mmoles) of hexyl isocyanate and heated at reflux for 24 hours. After removal of the solvent, the residue is dissolved in 100 ml of ethyl ether and the solution is neutralized with 3 ml of 10.6 N hydrogen chloride in ethanol. The resulting white precipitate is recrystallized from isopropanol to give 5.80 g (54.2% yield) of N-(2-dimethylaminoethyl)-N-(4,6-dimethyl-2-pyridyl)-N'-hexylurea hydrochloride, m.p. 175°–177°. Other compounds prepared by this method by replacing the hexyl isocyanate with the appropriate alkyl, cycloalkyl, or aryl isocyanate are listed in Table 1. The products are obtained as the free base when neutralization with hydrogen chloride in ethanol is omitted.

TABLE 1

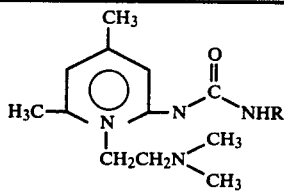

| Example | R | Salt | Recrystallization solvent | M.P. |
|---------|---|------|---------------------------|------|
| 2 | (CH$_3$)$_2$CH— | HCl | isopropanol | 198–200 |
| 3 | CH$_3$(CH$_2$)$_2$CH$_2$— | HCl | acetone | 205–207 dec. |
| 4 | CH$_3$CH$_2$CH$_2$— | HCl | isopropanol | 188–190 dec. |
| 5 | CH$_3$(HC$_2$)$_6$CH— | — | hexane | 53–54 |
| 6 | cyclohexyl | — | petroleum ether | 84–87 |
| 7 | CH$_3$ | | methyl cyclohexane | 73–75 |
| 8 | phenyl | 2HCl·1 H$_2$O | ethanol-dimethyl ether | 182 dec. |
| 9 | CF$_3$-phenyl | HCl | water | 201–203 |
| 10 | (CH$_3$)$_3$C— | HCl | isopropanol | 186–187 |

EXAMPLE 11

N,N-Diisopropyl-N'-(2-dimethylaminoethyl)-N'-(4,6-dimethyl-2-pyridyl)urea

A solution of 5.80 g (30.0 mmoles) of 2-(2-dimethylaminoethylamino)-4,6-dimethylpyridine (from Example 1, B) and 2.20 ml (30.0 mmoles) of triethylamine in 50 ml of benzene is dried by azeotropic distillation. After adding 4.91 g (30.0 mmoles) of diisopropylcarbamoyl chloride, the reaction mixture is heated at reflux for 24 hours. The crude product, after removal of solvent, is chromatographed on silica gel using 5% methanol in chloroform as eluant. Appropriate fractions are combined, the solvent removed and product distilled through a short path still to give 2.32 g (24.1% yield) of N,N-diisopropyl-N'-(2-dimethylaminoethyl)-N'-(4,6-dimethyl-2-pyridyl)urea as a colorless oil boiling at 148°/0.35 mm.

EXAMPLE 12

N,N-Dimethyl-N'-(2-dimethylaminoethyl)-N'-(4-methyl-2-pyridyl)urea Hydrochloride To a solution of 2-(2-dimethylaminoethylamino)-4-methylpyridine (8.07 g, 0.045 mole) and triethylamine (5.56 g, 0.055 ml) in 100 ml of dry benzene is added dimethylcarbamoyl chloride (5.37 g, 0.05 mole) with stirring. Then the mixture is heated at reflux on the steam bath for three hours. After the reaction mixture is cooled to about 10°, it is filtered. Removal of the solvent under reduced pressure gives an amber oil. The oil is diluted with 100 ml of ether and the solution is filtered. Removal of the ether under reduced pressure gives 11.3 g of amber oil (0.045 mole). This oil is dissolved in 6.5 ml (0.04 mole) of 6 N ethanolic hydrogen chloride. Dilution with ether precipitates a white solid. Filtration gives 10.7 g, m.p. 148°–149.5°. The product is recrystallized by dissolving in 10 ml of hot ethanol, seeding and slowly diluting with 100 ml of ether to yield 10.2 g, m.p. 148°–149° C. Yield 83%.

EXAMPLE 13

N,N-Dimethyl-N'-(2-dimethylaminoethyl)-N'-(5-methyl-2-pyridyl)urea Hydrochloride

A.

N-(2-Dimethylaminoethyl)-N-(5-methyl-2-pyridyl)acetamide

N-(5-Methyl-2-pyridyl)acetamide (75.0 g, 0.5 mole) is dissolved in 1000 ml of dry dimethylformamide and a 50% suspension of sodium hydride in mineral oil (24.0 g, 0.5 mole) is added under nitrogen with stirring in two portions over ¼ hour. The temperature rises to 40° and then is increased to 50°–55° to keep the salt in addition. Additional sodium hydride suspension (28.8 g, 0.6 mole) is added over 10 minutes followed by 2-dimethylaminoethyl chloride hydrochloride (86.5 g, 0.6 mole) added in small portions over ¼ hour. The temperature is moderated at 70° with occasional ice bath cooling. Then the mixture is stirred overnight at steam bath temperature. The reaction mixture is cooled and filtered. Removal of the dimethylformamide under reduced pressures gives a dark liquid. The product distills as a pale yellow liquid at 124°–128° at 0.6 mm, $n_{25}^D$ 1.5216. Weight obtained is 78 g.

B. 2-(2-Dimethylaminoethylamino)-5-methylpyridine

To N-(2-dimethylaminoethyl)-N-(5-methyl-2-pyridyl) acetamide (50.0 g, 0.226 mole) is added 200 ml of 5 N sodium hydroxide. The mixture is stirred rapidly at reflux for 16 hours. The mixture is cooled and the oil is extracted into ether. The ether extract is dried and evaporated under reduced pressure. Distillation of the residue gives a pale yellow liquid, b.p. 105°–112°, $n_{25}^D$ 1.5355. Weight obtained is 35 g.

C.

N,N-Dimethyl-N'-(2-dimethylaminoethyl)-N'-(5-methyl-2-pyridyl)urea Hydrochloride The title compound is obtained by following the procedure of Example 12 but substituting 8.07 g, (0.045 mole) of the product from part B above for 2(2-dimethylaminoethylamino)-4-methylpyridine and refluxing for 16 hours rather than 3 hours. Yield 10.3 g (84%), m.p. 148°–149°.

EXAMPLE 14

N,N-Dimethyl-N'-(2-dimethylaminoethyl)-N'-(6-amino-2-pyridyl)urea Hydrochloride

A.

N-(2-Dimethylaminoethyl)-N-(6-amino-2-pyridyl)acetamide

The title compound is obtained by following the procedure of part A of Example 13 but substituting an equivalent weight of N-(6-amino-2-pyridyl)acetamide for N-(5-methyl-2-pyridyl)acetamide. The product has b.p. 140°–178°/0.6 mm.

B. 2-(2-Dimethylaminoethylamino)-6-aminopyridine

This compound is obtained from N-(2-dimethylaminoethyl-N-(6-amino-2-pyridyl)acetamide as in the procedure of part B of Example 13. The product is collected at 120°–148° at 0.7 mm, $n_{25}^D$ 1.5680.

N,N-Dimethyl-N'-(2-dimethylaminoethyl)-N'-(6-amino-2-pyridyl)urea Hydrochloride

The title compound is obtained by following the procedure of Example 12 but substituting 0.045 mole of product from part B above for 2-(2-dimethylaminoethylamino)-4-methylpyridine and refluxing for 8 hours. The product is obtained in 29% yield, m.p. 111°–113°.

EXAMPLE 15

N,N-Dimethyl-N'-(2-dimethylaminoethyl)-N'-(5-chloro-2-pyridyl)urea Hydrochloride

A.

N-(2-Dimethylaminoethyl)-N-(5-chloro-2-pyridyl)acetamide

The title compound is obtained by following the procedure of part A of Example 13 but substituting an equivalent weight of N-(5-chloro-2-pyridyl)acetamide for N-(5-methyl-2-pyridyl)acetamide. The product has b.p. 123°–127°/0.1–0.3 mm.

B. 2-(2-Dimethylaminoethylamino)-5-chloropyridine

A solution of N-(2-dimethylaminoethyl)-N-(5-chloro-2-pyridyl)acetamide (45.5 g, 0.19 mole) in 200 ml of 6 N-hydrochloric acid is stirred at reflux for 16 hours. The excess hydrochloric acid is removed by evaporation under reduced pressure. The oily residue is treated with excess 10 N sodium hydroxide and the product is extracted into ether. The ether extract is dried, filtered and evaporated under reduced pressure. The residual oil is purified by distillation, b.p. 106°–111° at 0.7 mm $n_{25}^D$ 1.556. Weight obtained is 32.5 g.

C.

N,N-Dimethyl-N'-(2-dimethylaminoethyl)-N'-(5-chloro-2-pyridyl)urea Hydrochloride The title compound is obtained by following the procedure of Example 12 but substituting 0.045 mole of product from part B above for 2(2-dimethylaminoethylamino)-4-methylpyridine and refluxing for 18 hours. The product is obtained in 77% yield, m.p. 142.5°–143°.

EXAMPLE 16

N,N-Dimethyl-N'-(2-dimethylaminoethyl)-N'-(6-methyl-2-pyridyl)urea Hydrochloride The title compound is obtained by following the procedure of Example 13 except starting with N-(6-methyl-2-pyridyl)acetamide, in Part A, and refluxing for 2¾ hours in the procedure of Part C. The product is obtained in 72% yield, m.p. 129.5°–130.5°.

EXAMPLE 17

N,N-Dimethyl-N'-(2-dimethylaminoethyl)-N'-(3-methyl-2-pyridyl)urea Hydrochloride The title compound is obtained following the procedure of Example 13 except starting with N-(3-methyl-2-pyridyl)acetamide, in Part A, and refluxing for 24 hours in the procedure of Part C. The product is obtained in 81% yield, m.p. 135°–138°.

EXAMPLE 18

N,N-Dimethyl-N'-(2-diisopropylaminoethyl)-N'-(4,6-dimethyl-2-pyridyl)urea Monohydrochloride and Dihydrochloride

A. N,N-Dimethyl-N'-(4,6-dimethyl-2-pyridyl)urea

To a suspension of 57% sodium hydride in mineral oil (38.0 gm, 0.90 mole) in dry toluene (600 ml) at 75° under nitrogen atmosphere is added in small portions 2-amino-4,6-dimethylpyridine (52.5 gm, 0.43 mole). The reaction is heated to 100° for one hour and then cooled to 90°. A solution of dimethyl carbamoyl chloride (47.0 g, 0.43 m) in toluene (150 ml) is added dropwise over a one and one-half hour period. Stir for two hours and then cool to ambient temperature. Water (150 ml) is added, the organic layer separated, dried over anhydrous sodium sulfate filtered through charcoal and evaporated. The residue is triturated with cyclohexane (50 ml) and filtered to give analytically pure product (74.0 g., 85% yield), m.p. 105°–108° C.

B.

N,N-Dimethyl-N'-(2-diisopropylaminoethyl)-N'-(4,6-dimethyl-2-pyridyl)urea Dihydrochloride To a suspension of lithium hydride (0.65 g, 80 mmoles) in dry dioxane (65 ml) under nitrogen atmosphere is added N,N-dimethyl-N'-(4,6-dimethyl-2-pyridyl)urea (5.8 g, 30 mmoles) and the mixture is heated to reflux for three hours. 2-Diisopropylaminoethyl chloride hydrochloride (6.0 g, 30 mmoles) is added cautiously in small portions and refluxing continued for twenty-four hours. The reaction mixture is cooled, salts filtered off and solvent evaporated. The residue is dissolved in methylene chloride and the product is extracted into dilute aqueous hydrochloric acid (10%). This solution is filtered through charcoal, made basic with saturated sodium carbonate, and extracted with methylene chloride. The extract is dried over anhydrous sodium sulfate, filtered and evaporated. The crude product (8.3 g) is taken up in diethyl ether, insoluble material is removed by filtration and hydrogen chloride gas is bubbled into the filtrate. The precipitated salt is collected and recrystallized from isopropanol to give 5.2 g (44.0% yield) of product, m.p. 182°–186° C.

c. N,N-Dimethyl-N'-(2-diisopropylaminoethyl)-N'-(4,6-dimethyl-2-pyridyl)urea Monohydrochloride The addition of 1 equivalent of ethanolic hydrogen chloride to an ethereal solution of an additional 8.3 g. of crude product prepared as above gives the monohydrochloride salt which is recrystallized from ethanol-diethyl ether. The product melts at 192°–195°.

EXAMPLES 19–22

The compounds of the following general formula are made by the procedure of part B of the preceeding example except with substiution for 2-diisopropylaminoethyl chloride hydrochloride of the compound of the formula ClCH$_2$CH$_2$R wherein R is the group indicated in the following table.

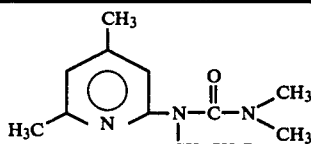

| Example | R | Analytical Data Formula | M.P. (solvent) | Yield % |
|---|---|---|---|---|
| 19 | N(CH$_2$CH$_2$CH$_2$CH$_3$)$_2$ | C$_{15}$H$_{26}$N$_4$O . 2HBr[a] | 161–164 (acetone) | 66 |
| 20 | CH$_3$ CH$_3$ N CH$_3$ CH$_3$ | C$_{21}$H$_{36}$N$_4$O[b] | 115–118° (ether) | 55 |
| 21 | N-(cyclohexyl)$_2$ | C$_{24}$H$_{40}$N$_4$O . 2HBr[a] + C$_{24}$H$_{40}$N$_4$O . HBr[a] | 209–212° 189–191° (acetone) | 49[c] |
| 22 | N(CH$_2$C$_6$H$_5$)$_2$ | C$_{26}$H$_{32}$N$_4$O . 2HBr[a] | 196–199° (acetone) | 56 |

[a] The hydrogen chloride gas of Example 16B is replaced by hydrogen bromide gas.
[b] Addition of hydrogen chloride gas in the procedure of Example 16B is omitted.
[c] Yield based on sum of mono and dihydrobromide salts.

EXAMPLE 23
N,N-Dimethyl-N'-(2-methylaminoethyl)-N'-(4,6-dimethyl-2-pyridyl)urea Dihydrobromide A solution of crude N,N-dimethyl-N'-[2-(benzylmethylamino)ethyl]-N'-(4,6-dimethyl-2-pyridyl)urea (prepared by the procedure of Example 18, Part B with substitution of 2-(benzylmethylamino)ethyl chloride for 2-diisopropylaminomethyl chloride and omitting the hydrogen chloride gas addition) (10.0 g, 29 mmoles) in glacial acetic acid (60 ml) containing 10% palladium-on-charcoal (3.0 g) is hydrogenated on a Parr apparatus until one equivalent of hydrogen is taken up (overnight). The catalyst is removed by filtration and the solvent is evaporated and the residue is dissolved in water. The solution is made basic with sodium carbonate, and extracted with methylene chloride. The extract is dried over anhydrous sodium sulfate, filtered through charcoal and evaporated. The residue is taken up in diethyl ether, and treated with hydrogen bromide gas. The precipitated salt is filtered and recrystallized from isopropanol to give 3.1 g (26% yield) of product, m.p. 170°–172°.

EXAMPLE 24
N,N-Dimethyl-N'-(3-dimethylaminopropyl)-N'-(4,6-dimethyl-2-pyridyl)urea Dihydrobromide A suspension of 57% sodium hydride in mineral oil (7.1 g, 0.17 mole) in a solution of 2-amino-4,6-dimethylpyridine (6.1 g, 0.05 mole) in dry toluene (60 ml) is heated at 100° for 1.5 hours under a nitrogen atmosphere. Dimethylcarbamoyl chloride (5.5 g, 0.05 mole) then is added cautiously dropwise. After one hour the reaction is cooled to ambient temperature and let stir overnight. 3-Dimethylaminopropyl chloride hydrochloride (7.9 g, 0.05 mole) is added in small portions and stirred at reflux for twenty-four hours. After cooling, ethanol (3 ml) is added, salts are filtered off and the solvent is evaporated. The residue is dissolved in methylene chloride, extracted into dilute aqueous hydrochloric acid, made basic with sodium carbonate solution and the product is extracted into methylene chloride. The solution is dried over anhydrous sodium sulfate, filtered through charcoal and evaporated to give a mixture (6.8 g) of 70% N-alkylated and 30% O-alkylated material. The residue is dissolved in diethyl ether and treated with hydrogen bromide gas. The precipitated salt is filtered off, digested in refluxing isopropanol, cooled and N,N-dimethyl-N'-(3-dimethylaminopropyl)-N'-(4,6-dimethyl-2-pyridyl)urea dihydrobromide is collected (2.7 g, 12% yield), m.p. 174°–176° C.

EXAMPLE 25
N,N-Dimethyl-N'-(2-dimethylaminoethyl)-N'-(4,6-dimethyl-2-pyridyl)urea Dihydrochloride 2-(2-Dimethylaminoethylamino)-4,6-dimethylpyridine (7.73 g, 0.04 mole) and triethylamine (4.8 g, 0.048 mole) are dissolved in 200 ml of anhydrous benzene. Dimethyl carbamoyl chloride (4.85 g, 0.045 mole) is added, the mixture stirred at room temperature for 2 hours and then refluxed four hours. After cooling and dilution with 200 ml of diethyl ether, the triethylamine hydrochloride is filtered off and the filtrate concentrated under vacuum. For purification the crude product is taken up in 200 ml diethyl ether and filtered thru Super-Cel. On addition of ethanolic hydrogen chloride to the filtrate, the product crystallizes and is filtered off to obtain 11 g of solid, m.p. 204°. Recrystallization from 150 ml ethanol and 250 ml diethyl ether yields 10.29 g, m.p. 205°–206° C. (d).

EXAMPLE 26

N,N-Dimethyl-N'-(2-dimethylaminoethyl)-N'-(2-pyridyl)urea Dihydrobromide

Following the procedure of Example 25 but substituting as starting material 0.4 mole of 2-(2-dimethylaminoethylamino)pyridine, and substituting hydrogen bromide for ethanolic hydrogen chloride the title compound is obtained, m.p. 170°(d).

EXAMPLE 27

1-[N-(2-Dimethylaminoethyl)-N-(4,6-dimethyl-2-pyridyl)carbamoyl]piperidine Dihydrochloride Hemihydrate Following the procedure of Example 25 but substituting 0.045 mole of 1-piperidine carbonyl chloride for dimethyl carbamoyl chloride, the title compound is obtained, m.p. 169°–171°.

EXAMPLE 28

4-Benzyl-1-[N-(2-dimethylaminoethyl)-N-(4,6-dimethyl-2-pyridyl)carbamoyl]piperazines esterhydrochloride Monohydrate Following the procedure of Example 25 but substituting 0.045 mole of 4-benzyl-1-piperazine carbonyl chloride for dimethyl carbamoyl chloride, the title compound is obtained, m.p. 200° (d).

EXAMPLE 29

N,N-Diethyl-N'-(2-dimethylaminoethyl)-N'-(4,6-dimethyl-2-pyridyl)urea dihydrobromide Sodium hydride, 57% in mineral oil, (2.319 g, 0.055 mole) is added to 150 ml anhydrous toluene in which 2-(2-dimethylaminoethylamino)-4,6-dimethylpyridine (9.66 g. 0.05 dimethyl-2-(2-dimethylaminoethylamino)-pyridine (9.66 g, 0.05 mole) is dissolved. While stirring under a stream of dry nitrogen the mixture is heated to 100° and maintained at this temperature until gas evolution abates, whereupon the mixture is then refluxed 1 hour. On cooling to 30°, diethylcarbamoyl chloride (7.45 g, 0.055 mole) in 25 ml of toluene is added and the mixture stirred ½ hour, then refluxed 1½ hours. On cooling a few ml of ethanol are added and the mixture is concentrated under vacuum. Dilute hydrochloric acid is added to the residue and the two phase system is extracted with hexane. The aqueous layer is separated and basified with 10 N sodium hydroxide with cooling. The oil that separates is extracted with methylene chloride. The organic extracts are backwashed with brine, dried over sodium sulfate and concentrated under vacuum. The residual oil is taken up in 1:1 diethyl ether:-hexane and filtered from insoluble matter. On reconcentration the crude product (11.9 g) is dissolved in diethyl ether and dry hydrogen bromide is passed into the solution. The supernatant is decanted from the precipitate which is then taken up in 65 ml of isopropanol. The insoluble matter is filtered off and discarded. Addition of 900 ml diethylether to the filtrate precipitates the product, 11.9 g, m.p. 134° (d).

EXAMPLE 30

N,N-Dimethyl-N'-(2-morpholinoethyl)-N'-(4,6-dimethyl-2-pyridyl)urea

A.

2-[2-(4-Morpholino)ethylamino]-4,6-dimethylpyridine

To N-(4,6-dimethyl-2-pyridyl)acetamide (20.5 g, 0.125 mole) dissolved in 400 ml dimethylformamide under nitrogen is added sodium hydride in mineral oil (50%) (6 g, 0.125 mole) in two portions with stirring. When bubbling ceases, 2-(4-morpholino)ethyl chloride hydrochloride (24.9 g, 0.134 ml is added and the mixture stirred 10 minutes. Sodium hydride (50%) (6.7 g, 0.14 M) is added in two portions over 20 minutes. The mixture is heated at 50°–51° for 1 hour and then at 90° for two hours. On cooling, 25 ml of ethanol is added and the mixture concentrated under vacuum. The residue is refluxed in 6 N hydrochloric acid overnight, cooled and extracted with heptane. The aqueous solution is made alkaline with 10 N sodium hydroxide and extracted with methylene chloride. The organic extracts are washed with brine, dried over sodium sulfate and concentrated under vacuum. The crude product is distilled and the fraction distilling at 135°–140°/0.1 mm collected. Weight. 17.1 g

B.

N,N-Dimethyl-N'-(2-morpholinoethyl)-N'-(4,6-dimethyl-2-pyridylurea

The title compound is obtained by following the procedure of Example 29 except substituting 0.05 mole of 2-(2-morpholinoethylamino)-4,6-dimethylpyridine (from Part A supra) for 2-(2-dimethylaminoethylamino)-4,6-dimethylpyridine and dimethylcarbamoyl chloride for diethylcarbamoyl chloride and omitting the addition of hydrogen bromide. The product melts at 74.5°–76.5°.

EXAMPLE 31

N,N-Diethyl-N'-(2-diethylaminoethyl)-N'-(4,6-dimethyl-2-pyridyl)urea Dihydrochloride A. 2-(2-Diethylaminoethylamino)-4,6-dimethylpyridine To 32.8 g (0.2 m) N-(4,6-dimethyl-2-pyridyl)acetamide dissolved in 300 ml dimethylformamide, sodium hydride (50%) (9.67 g 0.21 m) is added at 30°–40° in three portions with stirring. Ten minutes after this addition diethylaminoethylchloride hydrochloride (37.2 g, 0.216 m) is added and the mixture stirred 20 minutes. Sodium hydride (50%) (10.55 g, 0.229 M) is added in three portions at 40°–45°, the mixture stirred at 50°–55° for ½ hour and finally at 90° for 2½ hours. On cooling ethanol, 50 ml. followed by acetic acid, 25 ml, are added. The mixture is concentrated under vacuum, the residue dissolved in dilute hydrochloric acid, and extracted with hexane. The aqueous is made alkaline with sodium hydroxide, 10 N and extracted with methylene chloride. The organic extracts are washed with water, concentrated and the residue distilled. The fraction distilling at 127°–140°/1.3 mm, weight 35.5 g is collected, hydrolyzed by refluxing in sulfuric acid (85 ml), water (80 ml) and acetic acid (170 ml) for 18 hours. The mixture is cooled in an ice bath and sodium hydroxide solution equivalent to the sulfuric acid is added. Ethanol is added and the salts filtered off. The filtrate is concentrated under vacuum and the residue taken up in dilute sodium hydroxide. The mixture is extracted with methylene chloride, the organic extracts washed with brine, dried over sodium sulfate and concentrated to obtain the 2-(2-diethylaminoethylamino)-4,6-dimethylpyridine as an oil, weight 30 g.

B.
N,N-Diethyl-N'-(2-diethylaminoethyl)-N'-(4,6-dimethyl-2-pyridyl)urea Dihydrochloride The title compound is obtained by following the procedure of Example 29 except substituting 0.05 mole of 2-(2-diethylaminoethylamino)-4,6-dimethylpyridine from Part A supra for 2-(2-dimethylaminoethylamino)-4,6-dimethyl pyridine and neutralizing with ethanolic hydrogen chloride instead of hydrogen bromide. The product melts at 100°–105° (d).

EXAMPLE 32
N,N-Dimethyl-N'-(2-diethylaminoethyl)-N'-(4,6-dimethyl-2-pyridyl)urea The title compound is prepared following the procedure of Example 31 but employing 0.055 mole of dimethylcarbamoyl chloride in lieu of diethylcarbamoyl chloride in part B and omitting the addition of ethanolic hydrogen chloride. The product has a b.p. 126°–130°/0.3 mm.

EXAMPLE 33
N-(2-Diisopropylaminoethyl)-N-(4,6-dimethyl-2-pyridyl)-N'-methyl urea Dihydrochloride

A.
2-(2-Diisopropylaminoethylamino)-4,6-dimethylpyridine

The title compound is obtained following the procedure of part A of Example 31 except substituting an equivalent amount of diisopropylaminoethyl chloride for diethylaminoethyl chloride.

B.
N-(2-Diisopropylaminoethyl)-N-(4,6-dimethyl-2-pyridyl)N'-methylurea Dihydrochloride The title compound is prepared according to the procedure of Example 7 except substituting 0.0362 mole of 2-(2-diisopropylaminoethylamino)-4,6-dimethylpyridine from Part A for 2-(2-dimethylaminoethylamino)-4,6-dimethyl pyridine. The product melts at 179° (d).

EXAMPLE 34
N-{2-[N-(dimethylcarbamoyl)-N-(4,6-dimethyl-2-pyridyl)amino ethyl}-N,N,N-trimethylammonium iodide N,N-Dimethyl-N'-(2-dimethylaminoethyl)-N'-(4,6-dimethyl-2-pyridyl)urea dihydrochloride (8.83 g, 0.0261 M) from Example 23 is dissolved in water (50 ml) and the solution is made basic with 10 N sodium hydroxide. The oil that separates is extracted with methylene chloride, the organic extracts are washed with brine, dried over sodium sulfate and vacuum concentrated to obtain the free base. The free base is dissolved in 60 ml of diethyl ether chilled in an ice bath and methyl iodide (3.71 g, 0.026 mole) is added. After 1½ hours stirring, the cooling bath is removed and the mixture stirred overnight. On filtration 9.6 g of crude product is obtained. Recrystallization from 1:2 isopropanol:diethyl ether results in a product melting at 189°.

EXAMPLE 35
N,N-Dimethyl-N'-dimethylcarbamoyl-N'-(4,6-dimethyl-2-pyridyl)-1,2-ethanediamine-N-oxide dihydrochloride N,N-Dimethyl-N'-(2-dimethylaminoethyl)-N'-(4,6-dimethyl-2-pyridyl)urea dihydrochloride prepared as in Example 23 (8.43 g, 0.025 mole) is suspended in 10 ml water, cooled in an ice bath and 25 ml of 2 N sodium hydroxide are slowly added followed by 2.7 g (0.025 mole) of 31.5% hydrogen peroxide. After stirring, the solution at room temperature overnight, it is warmed at 45° for 24 hours. Upon cooling and addition of a catalytic amount of activated manganese dioxide, the mixture is filtered and concentrated under vacuum. The residue is taken up in ethanol, the sodium chloride filtered off, the filtrate acidified with dilute hydrochloric acid and reconcentrated. The residue is suspended in 30 ml isopropanol and the crude hygroscopic product (3.7 g, m.p. 164°–167° (d)) is filtered off. Recrystallization from 1:3 ethanol:diethyl ether gives a product melting at 173°–176° (d).

EXAMPLE 36
N-Methyl-N'-(2-dimethylaminoethyl)-N'-(4,6-dimethyl-2-pyridyl)-thiourea Hemihydrate The title compound is prepared according to the procedure of Example 7, Part C but substituting 0.0724 mole of methyl isothiocyanate for methyl isocyanate. The product melts at 63°–65° C.

EXAMPLE 37
N,N-Dimethyl-N'-(2-dimethylaminoethyl)-N'-(2-quinolyl)urea Hydrochloride The title compound is prepared according to the procedure of Example 12 except substituting 2-(2-dimethylaminoethylamino)quinoline for 2-(2-dimethylaminoethylamino)-4-methylpyridine and extending the period of reflux to 16 hours. The yield is 55%, m.p. 143°–144°.

EXAMPLE 38
N,N-Dimethyl-N'-(2-dimethylaminoethyl)-N'-(6-chloro-2-pyridyl)urea Hydrochloride A. 2-(2-Dimethylaminoethylamino)-6-chloro-pyridine A solution of 2,6-dichloropyridine (29.6 g., 0.20 mole) and unsymmetrical dimethylethylenediamine (52.9 g., 0.60 mole) in 100 ml of pyridine is stirred at reflux for 48 hours. The pyridine is removed under reduced pressure and the residual mixture is poured into water and made basic with excess sodium hydroxide. The product is extracted into ethyl acetate which is then concentrated and the residual oil is distilled. 2-(2-Dimethylaminoethylamino)-6-chloropyridine boiling at 104°–105° at 0.2 mm is collected in 70% yield.

B.
N,N-Dimethyl-N'-(2-dimethylaminoethyl)-N'-(6-chloro-2-pyridyl)urea Hydrochloride The title compund is obtained by following the procedure of Example 12 except substituting 2-(2-dimethylaminoethylamino)-6-chloropyridine from Part A for 2-(2-dimethylaminoethylamino)-4-methylpyridine and extending the period of reflux to 16 hours. The product is obtained in 79% yield, m.p. 135.5°–137°.

EXAMPLE 39

N,N-Dimethyl-N'-(2-dimethylaminoethyl)-N'-(6-dimethylaminomethyl-2-pyridyl)urea Dihydrochloride

A. 2-Chloro-6-dimethylaminomethylpyridine

To 2-chloro-6-methylpyridine (38.3 g, 0.30 mole) in 300 ml of carbon tetrachloride is added N-bromosuccinimide (67.0 g, 0.375 mole) and benzoyl peroxide (1.0 g). The mixture is stirred at reflux for 22 hours. Then it is cooled to 10° and is filtered. Into the carbon tetrachloride solution of crude 2-chloro-6-bromomethylpyridine is bubbled dimethylamine with ice bath cooling. The mixture is allowed to stand at room temperature overnight. After removal of the dimethylamine hydrobromide by filtration the carbon tetrachloride filtrate is concentrated in vacuo to a dark oil. The oil is taken up in hexane and the product is extracted into 6 N hydrochloric acid (0.30 mole). The acid extract is made alkaline with sodium hydroxide and the product is extracted into benzene. After removal of the benzene the product is distilled. The yield is 42%, b.p. 108°–110° at 3.3 mm, $n_{25}^D$ 1.5206.

B. 2-(2-Dimethylaminoethylamino)-6-dimethylaminomethylpyridine

2-Chloro-6-dimethylaminomethylpyridine (14 g., 0.0825 mole) and unsym-dimethylethylenediamine (21.8 g, 0.248 mole) in 10 ml of pyridine are heated at 180° for 8 hours in a bomb. The dark reaction mixture is stirred over 20 g of solid sodium hydroxide for 1 hour on a steam bath. Then the mixture is filtered. Distillation of the filtrate gives 6.5 g of product, b.p. 110°–11° at 0.1 mm, $n_D^{25}$ 1.5287.

C. N,N-Dimethyl-N'-(2-dimethylaminoethyl)-N'-(6-dimethylaminomethyl-2-pyridyl)urea Dihydrochloride The title compound is obtained following the procedure of Example 12 except starting with 6-dimethylaminomethyl-2-(2-dimethylaminoethylamino)pyridine in place of 2-(2-dimethylaminoethylamino)-4-methylpyridine and extending the period of reflux to 20 hours. The product is isolated as the dihydrochloride salt in 36% yield, m.p. 182°–183°.

EXAMPLE 40

N,N-Dimethyl-N'-(4-dimethylaminobutyl)-N'-(4,6-dimethyl-2-pyridyl)urea

A. N-(4-Chlorobutyl)-N-(4,6-dimethyl-2-pyridyl)acetamide

To N-(4,6-dimethyl-2-pyridyl)acetamide (49.2 g, 0.3 mole) dissolved in dimethylformamide (550 ml) is added sodium hydride in mineral oil (50%) (13.45 g., 0.32 mole) in portions at room temperature. When reaction is complete, the mixture is warmed with stirring to 45° and 1-bromo-4-chlorobutane (52.5 g., 0.306 mole) is added in one portion and stirred one hour on the steam bath. The reaction mixture is then cooled, acidified with hydrochloric acid and concentrated under vacuum. The residue is dissolved in water and extracted with diethyl ether. The aqueous layer is made basic with sodium hydroxide and extracted with ether. The combined etheral extracts are washed with brine, treated with charcoal, dried (sodium sulfate) and concentrated to obtain the product oil, weight 56.6 g.

B. 2-(4-Dimethylaminobutylamino)-4,6-dimethylpyridine

N-(4-Chlorobutyl)-N-(4,6-dimethyl-2-pyridyl)acetamide (28 g., 0.11 mole) is heated with dimethylamine (25 g., 0.55 mole) in 250 mole of ethanol in the presence of cuprous chloride (0.5 g.) for 6 hours at 100°. On cooling the mixture is treated with charcoal, filtered, and then concentrated under vacuum. The residue is taken up in dilute sodium hydroxide and the mixture extracted with diethyl ether, then methylene chloride. The organic extracts are concentrated after washing with water. The residue, weighing 26 g is then refluxed in 5 N sodium hydroxide (200 ml) overnight. On cooling the mixture is extracted with methylene chloride. The organic extracts are washed with brine, dried over sodium sulfate and concentrated. The residue is distilled to obtain the product oil, b.p. 137–142/1.2 mm.

C. N,N-Dimethyl-N'-(4-dimethylaminobutyl)-N'-(4,6-dimethyl-2-pyridyl)urea

To 2-(4-dimethylaminobutylamino)-4,6-dimethylpyridine (3.7 g. 0.00168 mole) dissolved in toluene (150 ml) is added sodium hydride in mineral oil (50%) (0.96 g., 0.002 mole. The mixture is refluxed with stirring under nitrogen for 3½ hours, cooled to 35°, and dimethylcarbamoyl chloride (2.15 g., 0.002 mole) in toluene (25 ml) is added. The mixture is then refluxed for 18 hours, cooled and extracted with dilute hydrochloric acid. The aqueous extracts are made alkaline with 10 N sodium hydroxide and extracted with diethyl ether then methylene chloride. The combined organic extracts are washed with brine, dried (sodium sulfate) and concentrated under vacuum. The residue is taken up in diethyl ether, filtered from insoluble matter and the filtrate concentrated. The residue is distilled and the product, a hygroscopic oil, is collected at 138°–141°/0.3 mm.

EXAMPLE 41

N,N-Dimethyl-N'-{2-[N-(2-hydroxyethyl)-N-methylamino]ethyl}-N'-(4,6-dimethyl-2-pyridyl)urea

A. 2-{2-[N-(2-Benzyloxyethyl)-N-methylamino]ethylamino}-4,6-dimethylpyridine To 24.5 g (0.149 mole) of N-(4,6-dimethyl-2-pyridyl)acetamide dissolved in 350 ml of dimethylformamide is added sodium hydride in mineral oil (50%) (7.2 g., 0.15 mole) in two portions with stirring, at room temperature. When reaction ceases, N-(2-benzyloxyethyl)-N-(2-chloroethyl)methylamine hydrochloride (24.5 g., 0.149 mole) is added in 2 portions. After bubbling ceases, the mixture is stirred at 50°–55° for 45 minutes and than heated on a steam bath for two hours. The mixture is cooled and concentrated under vacuum after 25 ml of acetic acid is added. The residue is taken up in dilute hydrochloric acid and extracted with hexane. The aqueous is made alkaline with 10 N sodium hydroxide and extracted with ether, then methylene chloride. The combined organic extracts are backwashed with brine, dried (sodium sulfate) and vacuum concentrated. The residue is distilled, the fraction boiling at 205°–215°/0.5 mm collected and this then refluxed in 5 N sodium hydroxide until hydrolysis is complete. On cooling, the mixture is extracted with toluene and then with methylene chloride. The combined organic extracts are washed with brine, dried and vacuum concentrated to obtain the product as an oil, weight 35 g.

B.
N,N-Dimethyl-N'-{2-[N-(2-benzyloxyethyl)-N-methylamino]ethyl}-N'-(4,6-dimethyl-2-pyridyl)urea 2-{2-[N-(2-Benzyloxyethyl)-N'-methylamino]ethylamino}-4,6-dimethylpyridine (32 g., 0.1022 mole) is dissolved in toluene (325 ml) under nitrogen and sodium hydride (50% in mineral oil) (5.4 g., 0.122 mole) is added. The mixture is heated with stirring at 105° for ½ hour and then refluxed 2 hours. On cooling to room temperature dimethylcarbamoyl chloride (13.2 g, 0.112 mole) in toluene (25 ml) is added and the mixture refluxed 48 hours, cooled, and concentrated under vacuum. The residue is taken up in dilute hydrochloric acid and extracted with heptane. The aqueous solution is made basic with sodium hydroxide and extracted with methylene chloride. The organic extracts are brine washed, dried over sodium sulfate and vacuum concentrated. The residue is taken up 1:1 diethyl ether:petroleum ether, treated with charcoal and filtered. On concentration, the product oil (37.4 g) is obtained and characterized by nmr.

C.
N,N-Dimethyl-N'-{2-[N-(2-hydroxyethyl)-N-methylamino]ethyl}-N'-(4,6-dimethyl-2-pyridyl)urea N,N-dimethyl-N'-{2-[N-(2-benzyloxyethyl)-N-methyl]aminoethyl}-N'-(4,6-dimethyl-2-pyridyl)urea (29.3 g., 0.763 mole) is dissolved in a mixture of 150 ml ethanol plus 19 ml 6 N ethanolic hydrochloric acid. Palladium on charcoal (6 g., 7.5%) is added and the mixture is shaken on a Parr apparatus until hydrogen uptake ceases. The mixture is filtered, the filtrate concentrated and the residue dissolved in water. The aqueous solution is made alkaline with sodium hydroxide (10 N) and extracted with toluene and then methylene chloride. The combined organic extracts are washed with brine, dried over sodium sulfate and concentrated under vacuum to obtain the crude product, weight 18.2 g. For purification, the hygroscopic product is distilled and the material distilling at 162°–165°/0.5 mm collected.

EXAMPLE 42
N,N-Dimethyl-N'-(2-dimethylaminoethyl)-N'-(4-trifluoromethyl-6-methyl-2-pyridyl)urea Hydrochloride

A.
2-(2-Dimethylaminoethylamino)-4-trifluoromethyl-6-methylpyridine

The title compound is obtained by following the procedure of Example 38, Part A except substituting 2-chloro-4-trifluoromethyl-6-methylpyridine for 2,6-dichloropyridine.

B.
N,N-Dimethyl-N'-(2-dimethylaminoethyl)-N'-(4-trifluoromethyl-6-methyl-2-pyridyl)urea Hydrochloride The title compound is obtained by following the procedure of Example 12 except substituting 2-(2-dimethylaminoethylamino)-4-trifluoromethyl-6-methylpyridine from Part A for 2-(2-dimethylaminoethylamino)-4-methylpyridine. This product melts at 152°–154°.

EXAMPLE 43
N,N-Dimethyl-N'-(2-dimethylaminoethyl)-N'-(6-methoxy-2-pyridyl)urea Hydrobromide

A. 2-(2-Dimethylaminoethylamino)-6-methoxy pyridine

A solution of 2-(2-dimethylaminoethylamino)-6-chloropyridine (10.0 g, 0.05 mole) in dimethylformamide (50 ml) containing sodium methoxide (3.5 gm, 0.065 mole) is heated at 110°–120° for two hours. The solution is cooled and the sodium chloride filtered. After removing the solvent in vacuo, the residue is dissolved in dilute hydrochloric acid (10%), washed with methylene chloride, made alkaline with sodium carbonate and the product is extracted into methylene chloride. After drying this solution over anhydrous sodium sulfate and filtering through charcoal, the solvent is removed under vacuum to give the oily product (7.9 g). This is used without further purification in the succeeding step.

B.
N,N-Dimethyl-N'-(2-dimethylaminoethyl)-N'-(6-methoxypyridyl)urea Hydrobromide The title compound is obtained by following the procedure of Example 12 except substituting 2-(2-dimethylaminoethylamino)-6-methoxypyridine from Part A, supra, for 2-(2-dimethylaminoethylamino)-4-methylpyridine and neutralizing with hydrogen bromide in place of ethanolic hydrogen chloride. The product melts at 138°–140°.

EXAMPLE 44
N,N-Dimethyl-N'-(2-dimethylaminoethyl)-N'-(6-methylthio-2-pyridyl)urea Hydrobromide

A.
2-(2-Dimethylaminoethylamino)-6-methylthiopyridine

The title compound is obtained by following the procedure of Example 43, Part A, except substituting sodium methyl mercaptide for sodium methoxide.

B.
N,N-Dimethyl-N'-(2-dimethylaminoethyl)-N'-(6-methylthio-2-pyridyl)urea Hydrobromide The title compound is obtained by following the procedure of Example 12 except substituting 2-(2-dimethylaminoethylamino)-6-methylthiopyridine from Part A, supra, for 2-(2-dimethylaminoethylamino)-4-methylpyridine and neutralizing with hydrogen bromide in place of ethanolic hydrogen chloride. The product melts at 148°–150°.

EXAMPLE 45
N,N-Dimethyl-N'-(2-dimethylaminoethyl)-N'-(6-cyano-2-pyridyl)urea Hydrobromide

A. 2-(2-Dimethylaminoethylamino)-6-cyanopyridine

The title compound is obtained by following the procedure of Example 38, Part A, except substituting 2-chloro-6-cyanopyridine for 2,6-dichloropyridine.

B.
N,N-Dimethyl-N'-(2-dimethylaminoethyl)-N'-(6-cyano-2-pyridyl)urea

The title compound is obtained by following the procedure of Example 12 except substituting 2-(2-dimethylaminoethylamino)-6-cyanopyridine from Part A, supra, for 2-(2-dimethylaminoethylamino)-4-methylpyridine.

EXAMPLE 46

N,N-Dimethyl-N'-(2-dimethylaminoethyl)-N'-(6-trifluoromethyl-2-pyridyl)urea

A. 2-(2-Dimethylaminoethylamino)-6-trifluoromethylpyridine

The title compound is obtained by following the procedure of Example 38, Part A, except substituting 2-fluoro-6-trifluoromethylpyridine for 2,6-dichloropyridine.

B. N,N-Dimethyl-N'-(2-dimethylaminoethyl)-N'-(6-trifluoromethyl-2-pyridyl)urea The title compound is obtained by following the procedure of Example 12 except substituting 2-(2-dimethylaminoethylamino)-6-trifluoromethylpyridine from Part A, supra, for 2-(2-dimethylaminoethylamino)-4-methylpyridine. The product boils at 105°-108° at 0.15 mm.

EXAMPLE 47

N,N-Dimethyl-N'-(2-dimethylaminoethyl)-N'-(6-dimethylamino-2-pyridyl)urea Hydrochloride

A. 2-Amino-6-dimethylaminopyridine

The title compound is obtained from the reaction of 2-amino-6-bromopyridine and dimethylamine in ethanol at 180° in a pressure vessel fro 36 hours. The product is distilled and then recrystallized from hexane, m.p. 58°-60°. The yield is 73%.

B. N-(6-Dimethylamino-2-pyridyl)acetamide

Acetylation of 2-amino-6-dimethylaminopyridine from Part A with acetic anhydride in benzene for 2 hours at reflux gives a quantative yield of the title compound. Melting point is 118°-119°.

C. N-(2-Dimethylaminoethyl)-N-(6-dimethylamino-2-pyridyl)-acetamide

The title compound is obtained as in the procedure of Example 13, Part A except substituting N-(6-dimethylamino-2-pyridyl)acetamide for N-(4,6-dimethyl-2-pyridyl)acetamide. The once distilled oil obtained is used in the following step without further purification.

D. 2-(2-Dimethylaminoethylamino)-6-dimethylaminopyridine

The title compound is obtained as in the procedure of Example 13, Part B except substituting N-(2-dimethylaminoethyl)-N-(6-dimethylamino-2-pyridyl)acetamide for N-(2-dimethylaminoethyl)-N-(5-methyl-2-pyridyl)acetamide.

E. N,N-Dimethyl-N'-(2-dimethylaminoethyl)-N'-(6-dimethylamino-2-pyridyl)urea Hydrochloride The title compound is obtained by following the procedure of Example 13, Part C but substituting 2-(2-dimethylaminoethylamino)-6-dimethylaminopyridine for 2-(2-dimethylaminoethylamino)-5-methylpyridine. The product melts at 143°-145°.

EXAMPLE 48

N,N-Dimethyl-N'-(2-dimethylaminoethyl)-N'-(5-nitro-2-pyridyl)urea Hydrochloride

A. 2-(2-Dimethylaminoethylamino)-5-nitropyridine

The title compound is obtained from 2-chloro-5-nitropyridine and unsymmetrical dimethylethylenediamine. This reaction proceeds exothermically at room temperature. Extraction and distillation as in Example 38, Part A gives a 60% yield.

B. N,N-Dimethyl-N'-(2-dimethylaminoethyl)-N'-(5-nitro-2-pyridyl)urea Hydrochloride The title compound is obtained by following the procedure of Example 12 except substituting 2-(2-dimethylaminoethylamino)-5-nitropyridine from Part A for 2-(2-dimethylaminoethylamino)-4-methylpyridine and increasing the period of reflux to 36 hours. The product melts at 188°-189°.

EXAMPLE 49

N-(2-Hydroxyethyl)-N'-(2-dimethylaminoethyl)-N'-(4,6-dimethyl-2-pyridyl)urea Dihydrate

A. 2-Acetoxyethyl isocyanate

A slurry of 2-acetoxyethylamine hydrochloride (20.0 g., 0.143 mole) in benzene (200 ml.) is saturated with phosgene. Then the mixture is heated at reflux for 7 hours while a slow stream of phosgene is passed through. After cooling to room temperature, the small amount of solid is removed by filtration. The filtrate is then concentrated in vacuum to give 13.3 g. of 2-acetoxyethyl isocyanate as a colorless oil.

The crude isocyanate is distilled through a 10 cm Vigreaux column to give pure product boiling at 61°-63°/2.75 mmg.

B. N-(2-Acetoxyethyl)-N'-(2-dimethylaminoethyl)-N'-(4,6-dimethyl-2-pyridyl)urea The title compound is obtained by following the procedure of Example 1, Part C except substituting 2-acetoxyethyl isocyanate for hexyl isocyanate and omitting the treatment with ethanolic hydrogen chloride.

C. N-(2-Hydroxyethyl)-N'-(2-dimethylaminoethyl)-N'-(4,6-dimethyl-2-pyridyl)urea Dihydrate A solution of N-(2-acetoxyethyl)-N'-(2-dimethylamino ethyl)-N'-(4,6-dimethyl-2-pyridyl)urea (11.5 g, 0.034 mole) in 1:1 ethanol-aqueous ammonia (300 ml.) is allowed to overnight at room temperature. The solvent is then removed under vacuum and the residue is crystallized from acetonitrile. The yield of crude product is 7.30 g, m.p. 173-176. Recrystallization from acetonitrile gives pure product melitng at 177°-179° C.

EXAMPLE 50

N-Methyl-N-phenyl-N'-(2-dimethylaminoethyl)-N'-(4,6-dimethyl-2-pyridyl)urea Dihydrochloride Sesterhydrate The title compound is prepared by following the procedure of Example 12 except substituting N-phenylcarbamoyl chloride for dimethylcarbamoyl chloride. The product melts at 215°-218°.

EXAMPLE 51

N,N-Dimethyl-N'-(2-dimethylaminoethyl)-N'-[4-(t-butoxycarbonyl)-6-chloro-2-pyridyl]urea Hydrochloride

A. t-Butyl 2,6-Dichloroisonicotinate

A solution of 2,6-dichloroisonicotinic acid (38.4 g, 0.20 mole) in thionyl chloride (60 ml.) and cyclohexane (100 ml) containing a few drops of dimethylformamide is heated at 80° for three hours. The solution is cooled and excess thionyl chloride and cyclohexane are removed in vacuo. The residue is dissolved in chloroform (40 ml.) and added dropwise to a solution of t-butanol (50 ml.) and N,N-dimethylaniline (40 ml.). The solution is heated at reflux for six hours, cooled, diluted with diethyl ether and washed successively with water, water containing 4 ml. of concentrated sulfuric acid, water, dilute sodium carbonate solution and dried over anhydrous sodium sulfate. The solvent is removed under vacuum and the residue is crystallized from a minimum amount of methanol to give 24 g. of product, m.p. 79°-81°.

B. 2-(2-Dimethylaminoethylamino)-4-(t-butoxycarbonyl)-6-chloropyridine

The title compound is obtained by following the procedure of Example 38, part A except substituting t-butyl 2,6-dichloroisonicotinate from Part A for 2,6-dichloropyridine and omitting the solvent pyridine. The melting point is 78°-81°.

C. N,N-Dimethyl-N'-(2-dimethylaminoethyl)-N'-[4-(t-butoxycarbonyl)-6-chloro-2-pyridyl]urea Hydrochloride The title compound is obtained by following the procedure of Example 12 except substituting 2-(2-dimethylaminoethylamino)-4-t-butoxy carbonyl-6-chloropyridine from Part B for 2-(2-dimethylaminoethylamino)-4-methylpyridine. The melting point is 175°-177°.

EXAMPLE 52

N,N-Dimethyl-N'-(2-dimethylaminoethyl)-N'-(6-methylsulfonyl-2-pyridyl)urea

A. 2,6-Bis-methylsulfonyl pyridine

A mixture of 2,6-dichloropyridine (14.8 g, 0.10 mole) and sodium methyl sulfenate (22.4 g., 0.22 mole) in dry dimethylformamide (150 ml.) is heated at reflux for six hours. The reaction mixture is cooled, sodium chloride is removed by filtration and the solvent is concentrated to a small volume and diluted with diethyl ether. The crystalline product is filtered, washed successively with water, ethanol and diethyl ether to remove traces of inorganic salts and dried in vacuo to give 16.5 g. This material is recrystallized from hot methanol, m.p. 192°-195°.

B. 2-(2-Dimethylaminoethyl)-6-methylsulfonyl pyridine

The title compound is obtained by following the procedure of Example 38, Part A except substituting 2,6-bis-methylsulfonyl pyridine for 2,6-dichloropyridine and omitting the solvent pyridine.

C. N,N-Dimethyl-N'-(2-dimethylaminoethyl)-N'-(6-methylsulfonyl-2-pyridyl)urea The title compound is obtained by following the procedure of Example 12 except substituting 2-(2-dimethylaminoethyl)-6-methylsulfonylpyridine from Part B for 2-(2-dimethylaminoethylamino)-4-methylpyridine. The product boils at 203°-206°/0.01 mm.

EXAMPLE 53

N,N-Dimethyl-N'-(2-dimethylaminoethyl)-N'-(4-trifluoromethyl-6-chloro-2-pyridyl)urea

A. 2-(2-Dimethylaminoethylamino)-4-trifluoromethyl-6-chloropyridine

The title compound is obtained by following the procedure of Example 38, Part A except substituting 4-trifluoromethyl-2,6-dichloropyridine for 2,6-dichloropyridine and omitting the solvent pyridine.

B. N,N-Dimethyl-N'-(2-dimethylaminoethyl)-N'-(4-trifluoromethyl-6-chloro-2-pyridyl)urea Hydrochloride The title compound is obtained by following the procedure of Example 12 except substituting 2-(2-dimethylaminoethylamino)-4-trifluoromethyl-6-chloropyridine from Part A for 2-(2-dimethylaminoethylamino)-4-methylpyridine. The product melts at 184°-196°.

EXAMPLE 54

N,N-Dimethyl-N'-(2-dimethylaminoethyl)-N'-(4-trifluoromethyl-6-methylamino-2-pyridyl)urea

A. 2-(2-Dimethylaminoethylamino)-4-trifluoromethyl-6-methylbenzylaminopyridine A mixture of 2-(2-dimethylaminoethylamino)-4-trifluoromethyl-6-chloropyridine (6.7 g., 0.025 mole) (from Example 53 Part A) and methylbenzylamine (11.0 g., 0.09 mole) is heated at 180° for 16 hours. The reaction mixture is cooled, diluted with water and the product is extracted into methylene chloride. The extract is dried over anhydrous sodium sulfate and the solvent then removed under vacuum. The residue is dissolved in diethyl ether and one equivalent of ethanolic hydrogen chloride is added. The diethyl ether is decanted and the oil is dissolved in water and passed through a pad of activated charcoal and the solution is discarded. The charcoal is digested with hot 10% sodium carbonate solution and the treated charcoal is extracted with hot chloroform several times. the extracts are combined, dried over anhydrous sodium sulfate and the solvent is removed in vacuo to give 5.1 g of oily product.

B. N,N-Dimethyl-N'-(2-dimethylaminoethyl)-N'-(4-trifluoromethyl-6-methylbenzylamino-2-pyridyl)urea The title compound is obtained by following the procedure of Example 12 except substituting 2-(2-dimethylaminoethylamino)-4-trifluoromethyl-6-methylbenzylamino pyridine from Part A for 2-(2-dimethylaminoethylamino)-4-methylpyridine.

C.
N,N-Dimethyl-N'(2-dimethylaminoethyl)-N'-(4-trifluoromethyl-6-methylamino-2-pyridyl)urea Two equivalents of ethanolic hydrogen chloride is added to a solution of N,N-dimethyl-N'-(2-dimethylaminoethyl)-N'-4-trifluoromethyl-benzylamino-2-pyridyl)urea (2.9 g., 0.068 mole) in absolute ethanol (30 ml.). This solution in the presence of 10% palladium-on-charcoal (0.4 g.) is hydrogenated in a Parr apparatus at 50 psi of hydrogen until one equivalent is taken up (1½ hours). The catalyst is removed by filtration and the solvent under vacuum. The residue is dissolved in water, made basic with sodium carbonate solution and extracted into methylene chloride. This solution is dried over anhydrous sodium sulfate and the solvent removed under vacuum. The product is crystallized from cyclohexane containing a small amount of n-butyl chloride (1.3 g, m.p. 96°–98°). This material is sublimed in vacuo to give pure product, m.p. 101°–103°.

EXAMPLE 55

N,N-Dimethyl-N'-(2-dimethylaminoethyl)-N'-(4-trifluoromethyl-2-pyridyl)urea Hydrochloride A.
2-(2-Dimethylaminoethylamino)-4-trifluoromethylpyridine A solution of 2-(2-dimethylaminoethylamino)-4-trifluoromethyl-6-chloropyridine (5.8 g., 0.022 mole) (from Example 53 Part A) in 2.5% potassium hydroxide in methanol (75 ml.) containing 5% palladium-on-calcium carbonate (0.5 g.) in hydrogenated in a Parr apparatus at 50 psi of hydrogen until 0.022 mole of hydrogen is taken up (24 hours). The catalyst is filtered and the solvent removed under vacuum. The residue is dissolved in water and the product is extracted into methylene chloride, dried over anhydrous sodium sulfate and evaporated to give the oily product (5.0 g.) which is used without further purification in the succeeding step.

B.
N,N-Dimethyl-N'-(2-dimethylaminoethyl)-N'-(4-trifluoromethyl-2-pyridyl)urea

The title compound is obtained by following the procedure of Example 12 except substituting 2-(2-dimethylaminoethylamino)-4-trifluoromethylpyridine from Part A for 2-(2-dimethylaminoethylamino)-4-methylpyridine and omitting the hydrogen chloride treatment. The melting point is 164°–166°.

EXAMPLE 56

N,N-Dimethyl-N'-(2-diisopropylaminoethyl)-N'-(4-trifluoromethyl-6-methyl-2-pyridyl)urea Hydrochloride A.
2-(2-Diisopropylaminoethylamino)-4-trifluoromethyl-6-methylpyridine The title compound is obtained by following the procedure of Example 38, Part A except substituting 2-chloro-4-trifluoromethyl-6-methylpyridine for 2,6-dichloropyridine for 2,6-dichloropyridine and N,N-diisopropylethylene diamine for N,N-dimethylethylene diamine. The product boils at 102°–103°/0.5 mm.

B.
N,N-Dimethyl-N'-(2-diisopropylaminoethyl)-N'-(4-trifluoromethyl-6-methyl-2-pyridyl)urea Hydrochloride The title compound is obtained by following the procedure of Example 29 except substituting 2-(2-diisopropylaminoethyl)-4-trifluoromethyl-6-methylpyridine from Part A for 2-(2-dimethylaminoethylamino)-4,6-methylpyridine. The product melts at 152°–154°.

EXAMPLE 57

N,N-Dimethyl-N'-(2-dimethylaminoethyl)-N'-(4-methyl-5-cyano-6-chloro-2-pyridyl)urea Hydrochloride A.
2-(2-Dimethylaminoethylamino)-4-methyl-5-cyano-6-chloropyridine and
2-(2-dimethylaminoethylamino)-3-cyano-4-methyl-6-chloropyridine To a stirred solution of unsymmetrical dimethylethylenediamine (53.0 g., 0.6 mole) in 50 ml. of pyridine under nitrogen atmosphere is added portionwise 2,6-dichloro-3-cyano-4-methylpyridine (37.4 g., 0.2 mole) with occasional cooling at 25° to 35° C. The reaction is left at room temperature over night. It is concentrated in vacuo giving a brown solid residue. This residue is dissolved in 200 ml of methylene chloride and is treated with aqueous sodium carbonate, washed with water, dried and concentrated in vacuo. The solid residue is suspended in 100 ml of cold petroleum ether. Filtration gives 24.2 g. of 2-(2-dimethylaminoethylamino)-4-methyl-5-cyano-6-chloropyridine. Recrystallization from n-butyl chloride gives pure material melting at 115.5°–118° C.

Concentration of the petroleum ether filtrate in vacuo gives 14.1 g of crude 2-(2-dimethylaminoethylamino)-3-cyano-4-methyl-6-chloropyridine as an amber oil which slowly solidifies. Crystallization from hexane with dry ice-acetone cooling gives 10.6 g. of white solid, melting point 43°–47° C.

B.
N,N-Dimethyl-N'-(2-dimethylaminoethyl)-N'-(4-methyl-5-cyano-6-chloro-2-pyridyl)urea Hydrochloride The title compound is obtained by following the procedure of Example 12 except substituting 2-(2-dimethylaminoethylamino)-4-methyl-5-cyano-6-chloropyridine from Part A for 2-(2-dimethylaminoethylamino)-4-methylpyridine. The product melts at 143.5°–145.5°.

EXAMPLE 58

N,N-Dimethyl-N'-(2-dimethylaminoethyl)-N'-(3-cyano-4-methyl-6-chloro-2-pyridyl)urea Hydrochloride The title compound is obtained by following the procedure of Example 12 except substituting 2-(2-dimethylaminoethylamino)-3-cyano-4-methyl-6-chloropyridine (the second isomer obtained in Example 57, Part A) for 2-(2-dimethylaminoethylamino)-4-methylpyridine. The product melts at 213°–214.5°.

EXAMPLE 59

N,N-Dimethyl-N'-(2-diisopropylaminoethyl)-N'-4-methyl-6-chloro-2-pyridyl)urea Hydrochloride

A.
2-(2-Diisopropylaminoethylamino)-4-methyl-5-cyano-6-chloropyridine

The title compound is isolated by following the procedure of Example 57, Part A, except substituting N,N-diisopropylethylene diamine for unsymmetrical-dimethylethylenediamine.

B.
2-(2-Diisopropylaminoethylamino)-4-methyl-6-chloropyridine

A solution of crude 2-(2-diisopropylaminoethylamino)-4-methyl-5-cyano-6-chloropyridine (4.0 g) in 20 ml of 50% (by volume) sulfuric acid is stirred at reflux for 16 hours over night. The solution is cooled and is cautiously poured into excess saturated sodium carbonate. The basic mixture is extracted with methylene chloride. After washing the extract with water, drying and filtering through activated carbon, the solvent is removed in vacuo. This gives 3.1 g of pale yellow oil which slowly solidifies. Extraction of the crude solid with hexane, cooling in dry ice-acetone and filtering gives 1.9 g. of white solid. The purified product melts at 64°-66° C.

C.
N,N-Dimethyl-N'-(2-diisopropylaminoethyl)-N'-(4-methyl-6-chloro-2-pyridyl)urea Hydrochloride The title compound is obtained by following the procedure of Example 29 except substituting 2-(2-diisopropylaminoethylamino)-4-methyl-6-chloropyridine from Part B for 2-(2-dimethylaminoethylamino)-4,6-dimethylpyridine and replacing hydrogen bromide with ethanolic hydrogen chloride. The product melts at 172°-175°.

EXAMPLE 60

N,N-Dimethyl-N'-(2-dimethylaminoethyl)-N'-(3,5-dichloro-2-pyridyl)urea Hydrochloride

A. N-(3,5-Dichloro-2-pyridyl)acetamide

The title compound is obtained by following the procedure of Example 47, Part B except substituting 2-amino-3,5-dichloropyridine for 2-amino-6-dimethylaminopyridine. The product melts at 152°-153°.

B.
N-(2-Dimethylaminoethyl)-N-(3,5-dichloro-2-pyridyl)acetamide

The title compound is obtained by following the procedure of Example 13, Part A except substituting N-(3,5-dichloro-2-pyridyl)acetamide for N-(5-methyl-2-pyridyl) acetamide.

C.
2-(2-Dimethylaminoethylamino)-3,5-dichloropyridine

The title compound is obtained by following the procedure of Example 15, Part B except substituting N-(2-dimethylaminoethyl)-N-(3,5-dichloro-2-pyridyl)acetamide for N-(2-dimethylaminoethyl)-N-(5-chloro-2-pyridyl)acetamide.

D.
N,N-Dimethyl-N'-(2-dimethylaminoethyl)-N'-(3,5-dichloro-2-pyridyl)urea Hydrochloride Under a nitrogen atmosphere, n-butyl lithium solution (45 ml., 0.073 mole) is added dropwise with stirring to a solution of 2-(2-dimethylaminoethylamino)-3,5-dichloro pyridine (16.4 g. 0.07 mole) in 150 ml of dry benzene at 25°-30° C. with occasional cooling over a ¾ hour period. After stirring an additional 15 minutes, dimethylcarbamoyl chloride (9.0 g., 0.084 mole) is added dropwise at 25° C. over ¼ hour. The reaction is stirred at room temperature for 2 hours and then at reflux for 16 hours over night.

After cooling, the reaction mixture is treated with saturated aqueous sodium chloride and the benzene layer is separated. The crude product is extracted from the benzene using 3 N hydrochloric acid. This aqueous solution is made basic and the product is extracted into diethyl ether, dried over sodium sulfate and the solvent removed to give 14.5 g. of crude amber oil which contains starting material. Purified product is obtained by carefully extracting an ether solution of the crude material with small portions of dilute hydrochloric acid. Combining the pure fractions separated after adjusting the pH to 11 and reextraction into ether gives 8.9 g. of oil. Treatment with an equivalent of ethanolic hydrogen chloride gives 7.3 g. of the monohydrochloride salt which is recrystallized from ethanol-ether, melting point 152°-154.5° C.

EXAMPLE 61

N,N-Dimethyl-N'-(2-diisopropylaminoethyl)-N'-(5-methyl-2-pyridyl)urea

A.
N-(2-Diisopropylaminoethyl)-N-(5-methyl-2-pyridyl)acetamide

The title compound is obtained by following the procedure of Example 13, Part A except substituting 2-diisopropylaminoethyl chloride hydrochloride for 2-dimethylaminoethyl chloride hydrochloride.

B. 2-(2-Diisopropylaminoethylamino)-5-methylpyridine

The title compound is obtained by following the procedure of Example 15, Part B except substituting N-(2-diisopropylaminoethyl)-N-(5-methyl-2-pyridyl)acetamide from Part A for N-(2-dimethylaminoethyl)-N-(5-chloro-2-pyridyl) acetamide.

C.
N,N-Dimethyl-N'-(2-diisopropylaminoethyl)-N'-(5-methyl-2-pyridyl)urea

The title compound is obtained by following the procedure of Example 60, Part D except substituting 2-(2-diisopropylaminoethylamino)-5-methylpyridine from Part B for 2-(2-dimethylaminoethylamino)-3,5-dichloropyridine. The product boils at 140°/0.05 mm.

EXAMPLE 62

N,N-Dimethyl-N'-(2-diisopropylaminoethyl)-N'-(5-chloro-2-pyridyl)urea

A.
N-(2-Diisopropylamonoethyl)-N-(5-chloro-2-pyridyl)acetamide

The title compound is obtained by following the procedure of Example 13, Part A except substituting N-(5-chloro-2-pyridyl)acetamide for N-(5-methyl-2-pyridyl) acetamide and 2-diisopropylaminoethylchloride hydrochloride for 2-dimethylaminoethylchloride hydrochloride.

B. 2-(2-Diisopropylaminoethylamino)-5-chloropyridine

The title compound is obtained by following the procedure of Example 15, Part B except substituting N-(2-diisopropylaminoethyl)-N-(5-chloro-2-pyridyl)-acetamide from Part A for N-(2-dimethylaminoethyl)-N-(5-chloro-2-pyridyl) acetamide.

C. N,N-Dimethyl-N'-(2-diisopropylaminoethyl)-N'-(5-chloro-2-pyridyl)urea

The title compound is obtained by following the procedure of Example 60, Part D except substituting 2-(2-diisopropylaminoethylamino)-5-chloropyridine from Part B for 2-(2-dimethylaminoethylamino)-3,5-dichloropyridine. The product boils at 147°/0.1 mm.

EXAMPLE 63

N,N-Dimethyl-N'-(2-methylisopropylaminoethyl)-N'-(4,6-dimethyl-2-pyridyl)urea Dihydrobromide

A. 2-Methylisopropylaminoethyl Chloride Hydrochloride

Thionyl chloride (57 ml. 0.775 M) is added with stirring and cooling (below 20°) to a solution of 2-methylisopropylaminoethanol (75 g., 0.64 M) dissolved in chloroform (300 ml.). The temperature is raised to 45° at which point gas evolution becomes evident and is maintained at 45°–55° for 1½ hour. The reaction mixture is refluxed for 2 hours. Then the mixture is cooled to 25° and ethanol (25 ml.) is added with stirring and the mixture is concentrated under vacuum. The residue is taken up in isopropanol (50 ml.) and ether (350 ml.) is added. The product is filtered and on drying, weights 107 g., melting point 114°–117°.

B. 2-(2-Methylisopropylaminoethylamino)-4,6-dimethylpyridine

The title compound is obtained by following the procedure of Example 1, Part A except substituting 2-methylisopropylaminoethyl chloride hydrochloride for 2-dimethylaminoethyl chloride hydrochloride and submitting this product directly to the pressure of Example 1, part B. The product boils at 105°–110°/0.3 mm.

C. N,N-Dimethyl-N'-(2-methylisopropylaminoethyl)-N'-(4,6-dimethyl-2-pyridyl)urea Dihydrobromide The title compound is obtained by following the procedure of Example 29 except substituting 2-(2-methylisopropylaminoethylamino)-4,6-dimethylpyridine for 2-(2-dimethylaminoethylamino)-4,6-dimethylpyridine. The product melts at 186°–188°.

EXAMPLE 64

N,N-Dimethyl-N'-(2-t-butylbenzylaminoethyl)-N'-(4,6-dimethyl-2-pyridyl)urea Dihydrobromide

A. 2-t-butylbenzylaminoethyl Chloride Hydrochloride

The title compound is obtained by following the procedure of Example 63, Part A except substituting 2-t-butyl benzylaminoethanol for 2-isopropylmethylaminoethanol. The product melts at 163°–165°.

B. 2-(2-t-butylbenzylaminoethylamino)-4,6-dimethylpyridine

The title compound is obtained by following the procedure of Example 1, Part A except substituting 2-t-butyl benzylaminoethylchloride hydrochloride for 2-dimethylaminoethyl chloride hydrochloride and submitting this product directly to the procedure of Example 1, Part B. This product boils at 169°–173°/0.5 mm.

C. N,N-Dimethyl-N'-(2-t-butylbenzylaminoethyl)-N'-(4,6-dimethyl-2-pyridyl)urea Dihydrobromide The title compound is obtained by following the procedure of Example 29 except substituting 2-(2-t-butylbenzylaminoethylamino)-4,6-dimethylpyridine from Part B for 2-(2-dimethylaminoethylamino)-4,6-dimethylpyridine. The product melts at 204° (decomposition).

EXAMPLE 65

N,N-Dimethyl-N'-(2-isopropylbenzylaminoethyl)-N'-(4,6-dimethyl-2-pyridyl)urea Dihydrobromide

A. 2-(2-Isopropylbenzylaminoethylamine)-4,6-dimethylpyridine

The title compound is obtained by following the procedure of Example 1, Part A except substituting 2-isopropylbenzylaminoethyl chloride hydrochloride for 2-dimethylaminoethylchloride hydrochloride and submitting this product directly to the procedure of Example 1, Part B. The product boils at 168°–172°/0.5 mm.

B. N,N-Dimethyl-N'-(2-isopropylbenzylaminoethyl)-N'-(4,6-dimethyl-2-pyridyl)urea Dihydrobromide The title compound is obtained by following the procedure of Example 29 except substituting 2-(2-isopropylbenzylaminoethylamino)-4.6-dimethylpyridine from Part A for 2-(2-dimethylaminoethylamino)-4,6-dimethylpyridine. The product melts at 203°–204°.

EXAMPLE 66

N,N-Dimethyl-N'-(2-isopropylaminoethyl)-N'-(4,6-dimethyl-2-pyridyl)-urea Hydrobromide Hydrate The title compound is obtained by following the procedure of Example 23, except substituting N,N-dimethyl-N'-(2-isopropylbenzylaminoethyl)-N'-(4,6-dimethyl-2-pyridyl) urea for N,N-dimethyl-N'-(2-benzylmethylaminoethyl)-N'-(4,6-dimethyl-2-pyridyl)urea and absolute ethanol for glacial acetic acid. The product melts at 128°–130°.

EXAMPLE 67

N,N-Dimethyl-N'-(2-t-butylaminoethyl)-N'-(4,6-dimethyl-2-pyridyl)urea Dihydrobromide The title compound is obtained by following the procedure of Example 23, except substituting N,N-dimethyl-N'-(2-t-butylbenzylaminoethyl)-N'-(4,6-dimethyl-2-pyridyl) urea for N,N-dimethyl-N'-(2-benzylmethylaminoethyl)-N'-(4,6-dimethyl-2-pyridyl)urea and absolute ethanol for glacial acetic acid. The product is a very hygroscopic solid.

EXAMPLE 68

N,N-Dimethyl-N'-(2-diisopropylaminoethyl)-N'-(5-chloro-4,6-dimethyl-2-pyridyl)urea Hydrochloride N,N-Dimethyl-N'-diisopropylaminoethyl)-N'-(4,6-dimethyl-2-pyridyl)urea (5.57 g., 0.017 mole) is dissolved in dry tetrahydrofuran (100 ml.), cooled under a nitrogen atmosphere to −10° and sulfuryl chloride (1.75 g., 0.013 mole) is added dropwise maintaining the internal temperature below −5°. The reaction is allowed to warm to 20° and is worked up by adding saturated sodium bicarbonate and extracting several times with diethyl ether. The combined extracts are dried over anhydrous sodium sulfate and the solvent removed in vacuo to give 5.73 g. of oil. This material was recycled through the above procedure four additional times using successively the following amounts of sulfuryl chloride: 1.21 g. (0.009 mole), 0.81 g. (0.006 mole), 0.54 g. (0.004 mole) and 0.40 g. (0.003 mole). The crude product (5.79 g) is chromatographed on aluminum (No. 2, 250 g.) eluting with chloroform and then on silica gel (900 g.) eluting with mixtures of 1:3 and 4:1 aqueous ammonia saturated chloroformchloroform. The combined fractions containing the product are washed with 5% sodium hydroxide solution, dried over anhydrous sodium sulfate and the solvent is removed to give 3.0 g. of oil which is dissolved in isopropanol (5 ml.) and treated with ethanolic hydrogen chloride (0.85 ml of 10.6 m solution) and diethyl ether (300 ml.). The collected product is recrystallized from isopropanol-diethyl ether to give 1.5 g., m.p. 164°-166° of title product.

EXAMPLE 69

N-(2-Dimethylaminoethyl)-N-(4,6-dimethyl-2-pyridyl)urea

A. N-(2-Dimethylaminoethyl)-N-(4,6-dimethyl-2-pyridyl) cyanamide

To a cooled, stirred solution of 2-(2-dimethyl)-aminoethylamino)-4,6-dimethylpyridine (15.4 g., 0.08 mole) and triethylamine (11.33 g., 0.112 mole) in tetrahydrofuran (150 ml.) is added slowly cyanogen bromide (11.86 g., 0.112 mole). After the addition is completed, the reaction is stirred at room temperature for one hour and then warmed to 50° C. for 30 minutes. The reaction is cooled to room temperature and cyanogen bromide (1.69 g., 0.16 mole) dissolved in 20 ml. of tetrahydrofuran is added. Stirring for 30 minutes at room temperature it is stirred at 50° for 1 hour. The mixture is cooled to room temperature and worked up by partition between ether (600 ml.) and water (100 ml.) Saturated sodium carbonate solution is added until strongly basic. After separating the ether layer the water layer is extracted with ether (4×50 ml.). The combined ether extracts are washed with water (2×50 ml.), dried over anhydrous sodium sulfate, filtered, and the solvent evaporated to leave 18.09 of oil. This oil is chromatographed on 150 g. of silica gel. The fractions containing the pure product are collected and the solvent evaporated to leave 1.29 g. of oil. This is used in the next step directly. A small sample was distilled and boils at 115°-130° C. at 0.05 mm.

B. N-(2-Dimethylaminoethyl)-N-(4,6-dimethyl-2-pyridyl)urea

A solution of N-(2-dimethylaminoethyl)-N-(4,6-dimethyl-2-pyridyl)cyanamide (5.66 g., 0.026 mole) in 6 N hydrochloric acid (60 ml.) is allowed to sit at room temperature for 1½ hour. The reaction solution was then cooled, made alkaline (pH about 11) with 50% sodium hydroxide solution, and extracted with ether. After washing with water and drying over anhydrous magnesium sulfate, the combined extracts are taken to dryness in vacuum. Recrystallization of the residue from hexane gives 3.90 g. of product urea, m.p. 88°-89° C.

EXAMPLE 70

N,N-Dimethyl-N'-(2-aminoethyl)-N'-(4,6-dimethyl-2-pyridyl)urea

A. 4,6-Dimethyl-2-pyridylamino acetonitrile

2-Amino-4,6-dimethylpyridine (17.6 g., 0.145 mole) is added to a solution of sodium hydroxymethane sulfonate (21.0 g., 0.145 mole) in boiling water (24 ml.). After 1½ hours, a solution of sodium cyanide (15.0 g., 0.305 mole) in water (30 ml.) is added. This mixture is allowed to reflux for an additional 3½ hours, then cooled and the product is extracted into methylene chloride. This solution is washed with water, dried over anhydrous sodium sulfate, filtered through a pad of charcoal and the solvent is removed in vacuo. The product, is crystallized from cyclohexane to give 37 g., m.p. 92°-93°.

B. N,N-Dimethyl-N'-(cyanomethyl)-N'-(4,6-dimethyl-2-pyridyl) urea

The title compound is obtained by following the procedure of Example 12 except substituting 4,6-dimethyl-2-pyridyl amino acetonitrile from A for 2-(2-dimethylaminoethylamino)-4-methylpyridine and refluxing 24 hours. The product mixture was recycled three times to complete this sluggish reaction.

C. N,N-Dimethyl-N'-(2-aminoethyl)-N'-(4,6-dimethyl-2-pyridyl) urea

A solution of N,N-dimethyl-N'-(cyanomethyl)-N'-(4,6-dimethyl-2-pyridyl)urea from Part B (5.3 g., 0.023 mole) in ethyl acetate (100 ml.) containing platinum oxide (0.8 g.) is hydrogenated in a Parr apparatus at 50 psi of hydrogen until the required amount is taken up (12 hours). The catalyst is filtered off and the solvent removed under vacuum to give 4.6 g. of oily product.

EXAMPLE 71

N,N-Dimethyl-N'-(2-dimethylaminoethyl)-N'-(5-amino-2-pyridyl) urea

A. 2-(2-Dimethylaminoethylamino)-5-nitropyridine

The title compound is obtained by following the procedure of Example 38, Part A except substituting 5-nitro-2-chloropyridine for 2,6-dichloropyridine.

B. N,N-Dimethyl-N'-(2-dimethylaminoethyl)-N'-(5-nitro-2-pyridyl)urea

The title compound is obtained by following the procedure of Example 12 except substituting 2-(2-dimethylaminoethylamino)-5-nitropyridine from Part A for 2-(2-dimethylaminoethylamino)-3,5-dichloropyridine.

C.
N,N-Dimethyl-N'-(2-dimethylaminoethyl)-N'-(5-amino-2-pyridyl)urea

N,N-Dimethyl-N'-(2-dimethylaminoethyl)-N'-(5-nitro-2-pyridyl)urea (9.68 g., 0.034 mole) is dissolved in absolute ethanol (50 ml.) containing 10% palladium-on-carbon and is hydrogenated at an initial 42 psi of hydrogen at ambient temperature for two hours. The reaction mixture is flushed with nitrogen and then is filtered under nitrogen. The filtrate is concentrated in vacuo on a steam bath to give a nearly colorless oil (8.05 g.) which partially solidifies on standing. Crystallization from acetonitrile yields 5.19 g. of the title compound, m.p. 118°–119° C.

EXAMPLE 72
N,N-Dimethyl-N'-(2-di-n-propylaminoethyl)-N'-(4,6-dimethyl-2-pyridyl)urea

A.
2-(2-Di-n-propylaminoethylamino)-4,6-dimethylpyridine

The title compound is obtained by following the procedure of Example 1, Part A except substituting 2-di-n-propylaminoethyl chloride hydrochloride for 2-dimethylaminoethyl chloride hydrochloride and submitting this product directly to the procedure of Example 1, Part B. The product boils at 133°–135°/1.3 mm.

B.
N,N-Dimethyl-N'-(2-di-n-propylaminoethyl)-N'-(4,6-dimethyl-2-pyridyl)urea The title compound is obtained by following the procedure of Example 29 except substituting 2-(2-di-n-propylaminoethylamino)-4,6-dimethylpyridine for 2-(2-dimethylaminoethylamino)-4,6-dimethylpyridine. The product boils at 142°–145°/0.4 mm.

EXAMPLE 73
N,N-Dimethyl-N'-(2-dimethylaminoethyl)-N'-(6-benzyloxy-2-pyridyl)urea Hydrochloride

A.
2-(2-Dimethylaminoethylamino-6-benzyloxypyridine

The title compound is obtained by following the procedure of Example 43, Part A except substituting sodium benzyloxide for sodium methoxide. The product boils at 158°–160°/0.25 mm.

B.
N,N-Dimethyl-N'-(2-dimethylaminoethyl)-N'-(6-benzyloxy-2-pyridyl)urea Hydrochloride The title compound is obtained by following the procedure of Example 12 except substituting 2-(2-dimethylaminoethylamino)-6-benzyloxypyridine from Part A for 2-(2-dimethylaminoethylamino)-4-methylpyridine. The product melts at 137°–138.5°.

EXAMPLE 74
N,N-Dimethyl-N'-(2-dimethylaminoethyl)-N'-(6-hydroxy-2-pyridyl)urea Hydrochloride A solution of N,N-dimethyl-N'-(2-dimethylaminoethyl)-N'-(6-benzyloxy-2-pyridyl)urea (from Example 73, Part B) (8.6 g., 0.025 mole) in 150 ml. of ethanol containing 10% palladium-on-carbon (0.5 g.) is hydrogenated at room temperature and 30 psi of hydrogen pressure using a Parr shaker. The catalyst is removed by filtration. Concentration of the filtrate in vacuo gives 6.8 g. of a colorless viscous gum. Treatment of the gum with ethanolic hydrogen chloride followed by addition of excess ether precipitates a gum which slowly solidifies. The yield of hydrochloride salt obtained is 5.6 g., m.p. 115°–117° C.

EXAMPLE 75
N,N-Dimethyl-N'-(2-diisopropylaminoethyl)-N'-(6-amino-2-pyridyl)urea Under a nitrogen atmosphere, n-butyl lithium solution (15.5 ml., 0.025 mole) is added dropwise with stirring to a dioxane (50 ml.) solution of N,N-dimethyl-N'-(6-amino-2-pyridyl)urea (4.5 g., 0.025 mole) at 10° C. Then 2-diisopropylaminoethyl chloride hydrochloride (55.5 g., 0.275 mole) is added followed by another portion of n-butyl lithium (15.5 ml., 0.025 mole). The mixture is heated at reflux over night. Ethanol (30 ml.) is added with cooling and the mixture is filtered and concentrated in vacuo. The residue is treated with ether and is filtered to remove salts. Removal of the ether in vacuo gives 5.1 g. of viscous oil. The crude oil is taken up in hexane, filtered and cooled to −25° C. Filtration gives 1.5 g. of white solid, m.p. 86°–88° C.

EXAMPLE 76
N,N-Dimethyl-N'-(2-diisopropylaminoethyl)-N'-(6-chloro-2-pyridyl)urea Hydrochloride A. 2-(2-Diisopropylaminoethylamino)-6-chloropyridine The title compound is obtained by following the procedure of Example 38, Part A except substituting N,N-diisopropylethylenediamine for unsymmetrical dimethylenediamine. The product boils at 127°–129°/0.5 mm.

B.
N,N-Dimethyl-N'-(2-diisopropylaminoethyl)-N'-(6-chloro-2-pyridyl)urea Hydrochloride The title compound is obtained by following the procedure of Example 29 except substituting 2-(2-diisopropylaminoethylamino)-6-chloropyridine from Part A for 2-(2-dimethylaminoethylamino)-4,6-dimethylpyridine and substituting ethanolic hydrogen chloride for hydrogen bromide. The product melts at 143.5°–145.5°.

EXAMPLE 77
N,N-Dimethyl-N'-(2-dimethylaminoethyl)-N'-(4-methyl-6-chloro-2-pyridyl)urea Hydrochloride

A.
2-(2-Dimethylaminoethylamino)-4-methyl-6-chloropyridine

The title compound is obtained by following the procedure of Example 38 except substituting 2,6-dichloro-4-methylpyridine for 2,6-dichloropyridine. The product boils at 113°–115°/0.2 mm.

B.
N,N-Dimethyl-N'-(2-dimethylaminoethyl)-N'-(4-methyl-6-chloro-2-pyridyl)urea Hydrochloride The title compound is obtained by following the procedure of Example 12 except substituting 2-(2-dimethylaminoethylamino)-4-methyl-6-chloropyridine for 2-(2-dimethylaminoethylamino)-4-methylpyridine. The product melts at 144°–145.5°.

EXAMPLE 78

N,N-Dimethyl-N'-(2-diisopropylaminoethyl)-N'-(4-methyl-2-pyridyl)urea Hydrochloride

A.

2-(2-Diisopropylaminoethylamino)-4-methylpyridine

The title compound is obtained by following the procedure of Example 1, Part A, except substituting N-(4-methyl-2-pyridyl)acetamide for N-(4,6-dimethyl-2-pyridyl) acetamide and 2-diisopropylaminoethyl chloride hydrochloride for 2-dimethylaminoethyl chloride hydrochloride and submitting this product directly to the procedure of Example 15, Part B. The product boils at 130°–131°/0.6 mm.

B.

N,N-Dimethyl-N'-(2-diisopropylaminoethyl)-N'-(4-methyl-2-pyridyl)urea Hydrochloride The title compound is obtained by following the procedure of Example 29 except substituting 2-(2-diisopropylaminoethylamino)-4-methylpyridine for 2-(2-dimethylaminoethylamino)-4,6-dimethylpyridine and substituting ethanolic hydrogen chloride for hydrogen bromide. The product melts at 133°–136°.

EXAMPLE 79

N,N-Dimethyl-N'-(2-dimethylaminoethyl)-N'-(4-methyl-6-amino-2-pyridyl)urea

A.

2-(2-Dimethylaminoethylamino)-4-methyl-6-aminopyridine

A mixture of 2-(2-dimethylaminoethylamino)-4-methyl-6-chloropyridine (from Example 77, Part A) (21.4 g., 0.1 mole), liquid ammonia (85 g) and copper sulfate catalyst (1.0 g) in 150 ml. ethanol is heated at 200° C. for 48 hours in a pressure vessel. The cooled reaction mixture is filtered and concentrated in vacuo. The residual oil is dissolved in 125 ml of chloroform, washed with excess sodium hydroxide and then with saturated sodium chloride solution, dried, filtered and concentrated in vacuo. The 16.0 g. of crude oil obtained is taken up in 100 ml of ether, filtered and extracted into dilute hydrochoric acid. The acidic extract is made basic and the product is extracted into ether. After drying and removing the ether in vacuo, the product (8.0 g.) is distilled. Purified material is collected at 125°–128° C. at 0.4 mm.

B.

N,N-Dimethyl-N'-(2-dimethylaminoethyl)-N'-(4-methyl-2-pyridyl)urea

The title compound is obtained by following the procedure of Example 12 except substituting 2-(2-dimethylaminoethylamino)-4-methyl-6-aminopyridine from Part A for 2-(2-dimethylaminoethylamino)-4-methylpyridine and omitting the treatment with ethanolic hydrogen chloride. The product melts at 100°–102°.

EXAMPLE 80

N,N-Dimethyl-N'-(2-dimethylamino-2-methylpropyl)-N'-(4,6-dimethyl-2-pyridyl)urea

A.

2-(2-Dimethylamino-2-methylpropylamino)-4,6-dimethyl pyridine

The title compound is obtained by following the procedure of Example 1, Part A except substituting 2-dimethylamino-2-methylpropylchloride hydrochloride for 2-dimethylaminoethyl chloride hydrochloride and submitting this product directly to the procedure of Example 1, Part B. The product boils at 110°–119°/0.8 mm.

B.

N,N-Dimethyl-N'-(2-dimethylamino-2-methylpropyl)-N'-(4,6-dimethyl-2-pyridyl)urea The title compound is obtained by following the procedure of Example 29 except substituting 2-(2-dimethylamino-2-methylpropylamino)-4,6-dimethylpyridine for 2-(2-dimethylaminoethylamine)-4,6-dimethylpyridine. The product melts at 69°–71°.

EXAMPLE 81

N,N-Dimethyl-N'-(3-dimethylamino-2-methylpropyl)-N'-(4,6-dimethyl-2-pyridyl)urea

A.

2-(3-Dimethylamino-2-methylpropylamine)-4,6-dimethylpyridine

The title compound is obtained by following the procedure of Example 1, Part A except substituting 3-dimethylamino-2-methylpropyl chloride hydrochloride for 2-dimethylaminoethyl chloride hydrochloride and submitting this product directly to the procedure of Example 1, Part B. The product boils at 104°–106°/0.3 mm.

B.

N,N-Dimethyl-N'-(3-dimethylamino-2-methylpropyl)-N'-(4,6-dimethyl-2-pyridyl)urea The title compound is obtained by following the procedure of Example 29 except substituting 2-(3-dimethylamino-2-methylpropylamino)-4,6-dimethylpyridine for 2-(2-dimethylaminoethylamino)-4,6-dimethylpyridine. The product boils at 131°–133°/0.5 mm.

EXAMPLE 82

N,N-Dimethyl-N'-(2-diisopropylaminoethyl)-N'-(4,6-dimethyl-2-pyridyl)thiourea

A solution of 4.99 g. (20.0 mmoles) of 2-diisopropylaminoethylamino-4,6-dimethylpyridine in 50 ml of dry tetrahydrofuran is allowed to react with 13.6 ml. (22.0 mmole) of 1.62 M butyl lithium in hexane. Then 2.72 g. (22.0 mmole) of dimethyl thiocarbamoyl chloride in 25 ml. of dry tetrahydrofuran is added over 20 minutes with ice cooling. The reaction mixture is allowed to stir overnight at room temperature. After quenching with water, the product is extracted into ether. The ether extract is washed with water and saturated sodium chloride solutions and dried over magnesium sulfate. Crude product is obtained as a brown oil weighing 6.19 g.

The crude product was chromatographed on silica gel, eluting with 5% methanol in chloroform. After combining the appropriate fractions, the solvent is removed in vacuum and the residue distilled through a short path still. There is obtained 1.34 g. (20% yield) of title product boiling at 189°–192°/0.5 mm.,

EXAMPLE 83

N,N-Dimethyl-N'-(2-diisopropylaminoethyl)-N'-(4-ethyl-2-pyridyl)urea Dihydrochloride

A. N-(4-Ethyl-2-pyridyl)acetamide

The title compound is obtained by following the procedure of Example 47, Part B, except substituting 2-amino-4-ethylpyridine for 2-amino-6-dimethylaminopyridine. The melting point is 142°–146°.

B. N-(2-Disopropylaminoethyl)-N-(4-ethyl-2-pyridyl)acetamide

The title compound is obtained by following the procedure of Example 13, Part A, except substituting N-(4-ethyl-2-pyridyl)acetamide and 2-diisopropylaminoethyl chloride hydrochloride for N-(5-methyl-2-pyridyl)acetamide and 2-dimethylaminoethyl chloride hydrochloride, respectively.

C. 2-(2-Diisopropylaminoethylamino)-4-ethylpyridine

The title compound is obtained by following the procedure of Example 15, Part B, except substituting N-(2-diisopropylaminoethyl)-N-(4-ethyl-2-pyridyl)acetamide from Part B above for N-(2-dimethylaminoethyl)-N-(5-chloro-2-pyridyl)acetamide. The product has b.p. 124°–125°/0.4 mm.

D. N,N-Dimethyl-N'-(2-diisopropylaminoethyl)-N'-(4-ethyl-2-pyridyl)urea Dihydrochloride The title compound is obtained by following the procedure of Example 29 except substituting 2-(2-diisopropylaminoethylamino)-4-ethylpyridine for 2-(2-dimethylaminoethylamino)-4,6-dimethylpyridine. The hydrogen bromide is replaced by ethanolic hydrogen chloride to give the product which melts at 159.5°–161.5°.

EXAMPLE 84

N,N-Dimethyl-N'-(2-diisopropylaminoethyl)-N'-(4-t-butyl-2-pyridyl)urea Hydrochloride

A. N-(4-t-Butyl-2-pyridyl)acetamide

The title compound is obtained by following the procedure of Example 47, Part B, except substituting 2-amino-4-t-butyl pyridine for 2-amino-6-dimethylaminopyridine. The melting point is 118°–119.5°.

B. N-(2-Diisopropylaminoethyl)-N-(4-t-butyl-2-pyridyl)acetamide

The title compound is obtained by following the procedure of Example 13, Part A, except substituting N-(4-t-butyl-2-pyridyl)acetamide and 2-diisopropylaminoethyl chloride hydrochloride for N-(5-methyl-2-pyridyl)acetamide and 2-dimethylaminoethyl chloride hydrochloride, respectively.

C. 2-(2-Diisopropylaminoethylamino)-4-t-butylpyridine

The title compound is obtained by following the procedure of Example 15, Part B, except substituting N-(2-diisopropylaminoethyl)-N-(4-t-butyl-2-pyridyl)acetamide from Part B above for N-(2-dimethylaminoethyl)-N-(5-chloro-2-pyridyl)acetamide. The product has b.p. 135°–136°/0.6 mm.

D. N,N-Dimethyl-N'-(2-diisopropylaminoethyl)-N'-(4-t-butyl-2-pyridyl)urea Hydrochloride The title compound is obtained by following the procedure of Example 60, Part D, except substituting 2-(2-diisopropylaminoethylamino)-4-t-butylpyridine from Part C above for 2-(2-dimethylaminoethylamino)-3,5-dichloropyridine. The product melts at 183°–184.5°.

EXAMPLE 85

N,N-Dimethyl-N'-(2-diisopropylaminoethyl)-N'-(6-amino-5-chloro-2-pyridyl)urea Hydrochloride

A. Ethyl N-(6-amino-5-chloro-2-pyridyl)carbamate

A solution of 3-chloro-2,6-diaminopyridine (129 g. 0.9 mole) in 1000 ml. of tetrahydrofuran and 250 ml. of water containing sodium bicarbonate (84 g., 1.0 mole) is stirred at 0° C. while adding ethyl chloroformate (114 g. 1.05 mole) dropwise over ½ hour. The mixture is stirred at 0° C. over night. The dark solution is filtered through activated carbon and the organic layer of the filtrate is separated, dried and concentrated in vacuo. The residual oil is taken up in ether, washed with 5 N sodium hydroxide and with saturated sodium chloride solution, dried and concentrated in vacuo. A light amber oil (162 g.) which solidifies when triturated in petroleum ether is obtained. The solid is purified by extracting into boiling hexane (10×300 ml) and cooling the extracts to give 131.6 g. of white solid, m.p. 66°–70°.

B. N,N-Dimethyl-N'-(6-amino-5-chloro-2-pyridyl)urea

A mixture of ethyl N-(6-amino-5-chloro-2-pyridyl)carbamate (64.7 g., 0.3 mole), dimethylamine (45 g., 1.0 mole) and 300 ml. of ethanol is heated at 120° C. for 24 hours in a pressure vessel. The reaction mixture is then concentrated in vacuo and 68 g. of brown solid is obtained. Recrystallization from n-butyl chloride gives pure material, m.p. 139°–141°

C. N,N-Dimethyl-N'-(2-diisopropylaminoethyl)-N'-(6-amino-5-chloro-2-pyridyl)urea Hydrochloride The title compound is obtained by following the procedure of Example 18, Part B, except substituting N,N-dimethyl-N'-(6-amino-5-chloro-2-pyridyl)urea from Part B above, for N,N-dimethyl-N'-(4,6-dimethyl-2-pyridyl)urea.

EXAMPLE 86

N,N-Dimethyl-N'-(2-dimethylaminoethyl)-N'-(5-carbamoyl-2-pyridyl)urea Hydrochloride

A. 2-(2-Dimethylaminoethylamino)-5-carbamoylpyridine

The title compound is obtained by following the procedure of Example 38 except substituting 6-chloronicotinamide for 2,6-dichloropyridine and omitting the solvent pyridine. The product melts at 125°–128°.

B. N,N-Dimethyl-N'-(2-dimethylaminoethyl)-N'-(5-carbamoyl-2-pyridyl)urea Hydrochloride The title compound is obtained by following the procedure of Example 12 except substituting 2-(2-dimethylaminoethylamino)-5-carbamoylpyridine from Part A above for 2-(2-dimethylaminoethylamino-4-methyl-pyridine.

EXAMPLE 87

N,N-Dimethyl-N'-(2-dimethylaminoethyl)-N'-(3-pyridyl)urea Hydrochloride

A. N-(2-Dimethylaminoethyl)-N-(3-pyridyl)acetamide

The title compound is prepared by following the procedure of Example 13, Part A except substituting N-(3-pyridyl)acetamide for N-(5-methyl-2-pyridyl-)acetamide.

B. 3-(2-Dimethylaminoethylamino)pyridine

The title compound is prepared by following the procedure of Example 15, Part B, except substituting N-(2-dimethylaminoethyl)-N-(3-pyridyl)acetamide from Part A above for N-(2-dimethylaminoethyl)-N-(5-chloro-2-pyridyl)acetamide. The product has b.p. 87°–90°/0.4 mm.

C. N,N-Dimethyl-N'-(2-dimethylaminoethyl)-N'-(3-pyridyl)urea Hydrochloride

The title compound is prepared by following the procedure of Example 12 except substituting 3-(2-dimethylaminoethylamino)pyridine for 2-(2-dimethylaminoethylamino)-4-methylpyridine. The product melts at 142°–144°.

EXAMPLES 88–110

Compounds of the general formula

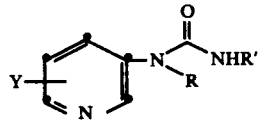

(Examples 88–107) are prepared by the following sequence of reactions: 3-aminopyridines of the general formula

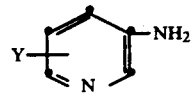

wherein Y is listed in column A of Table I are reacted with acetic anhydride by following the procedure of Example 47, Part B. The resulting acetamides are then alkylated with the reagents RCl, where R is listed in column B, according to the procedure of Example 13, Part A, and hydrolyzed according to the procedure of Example 15, Part B, to give compounds of the general formula

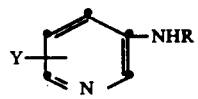

wherein Y and R have the same meaning as in columns A and B, respectively. These compounds are reacted with an isocyanate or isothiocyanate R'N=C=X wherein R' and X are listed in column C, by following the procedure of Example 1, Part C, to give the corresponding pyridylureas of the general formula

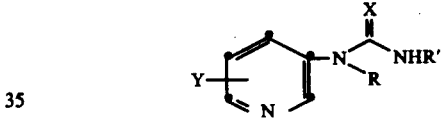

where Y, R, R' and X have the same meaning as in columns A, B and C, respectively of Table I.

In addition the nitro-substituted pyridylureas (Examples 105–107) are reduced to give the corresponding amino-substituted pyridylureas (Examples 108–110) by following the procedure of Example 71, Part C.

TABLE I

| | A | B | C | |
|---|---|---|---|---|
| EXAMPLE | Y | R | R' | X |
| 88 | 5-CH$_3$ | —CH$_2$CH$_2$NCH$_3$<br>\|<br>CH$_2$C$_6$H$_5$ | —CH$_3$ | 0 |
| 89 | 6-CH$_3$ | —CH$_2$CH$_2$N(CH$_3$)$_2$ | —CH$_2$CH$_2$CH$_3$ | 0 |
| 90 | 6-CH$_2$CH$_2$CH$_2$CH$_3$ | —CH$_2$CH$_2$N(CH$_2$CH$_3$)$_2$ | —CH(CH$_3$)$_2$ | 0 |
| 91 | 6-C(CH$_3$)$_3$ | —CH$_2$CH$_2$N(CH$_2$CH$_2$CH$_3$)$_2$ | (cyclohexyl) | 0 |
| 92 | 4-OCH$_3$ | —CH$_2$CH$_2$NCH(CH$_3$)$_2$<br>\|<br>CH$_3$ | —C$_6$H$_5$ | 0 |
| 93 | 5-OCH$_3$ | —CH$_2$CHN(CH$_3$)$_2$<br>\|<br>CH$_3$ | —CH$_3$ | S |
| 94 | 4-SCH$_3$ | —CH$_2$C(CH$_3$)$_2$N(CH$_3$)$_2$ | —CH$_2$(CH$_2$)$_2$CH$_3$ | 0 |
| 95 | 6-SCH$_3$ | —CH$_2$CH$_2$N(CH$_3$)$_2$ | —CH$_2$(CH$_2$)$_6$CH$_3$ | 0 |
| 96 | 6-N(CH$_3$)$_2$ | —CH$_2$CH$_2$N(piperidinyl)$_2$ | —CH$_3$ | 0 |
| 97 | 6-N(CH$_2$CH$_3$)$_2$ | —CH$_2$CH$_2$N(CH$_2$C$_6$H$_5$)$_2$ | —CH$_3$ | S |

TABLE I-continued

| EXAMPLE | A<br>Y | B<br>R | C<br>R' | X |
|---|---|---|---|---|
| 98 | 2-Cl | —CH₂CH₂NCH(CH₃)₂<br>           \|<br>          CH₃ | —CH(CH₃)₂ | O |
| 99 | 5-Cl | —CH₂CH₂N⟨morpholino⟩ | —CH₂CH₂CH₃ | O |
| 100 | 6-SO₂CH₃ | —CH₂CH₂N⟨piperidino⟩ | —C₆H₅ | O |
| 101 | 2,6-diCH₃ | —CH₂CH₂N(CH₃)₂ | —CH₂CH₂CH₃ | O |
| 102 | 2-Cl, 5-CH₃ | —CH₂CH₂CH₂N(CH₃)₂ | —CH₃ | S |
| 103 | 2-Cl, 6-CH₃ | —CH₂CH₂N⟨piperidino⟩ | —C₆H₁₁ (cyclohexyl) | O |
| 104 | 2,5,6-triCH₃ | —CH₂CH₂N(CH₂CH₃)₂ | —C₆H₁₁ (cyclohexyl) | O |
| 105 | 2-NO₃ | —CH₂CH₂N(CH₃)₂ | —C₆H₅ | O |
| 106 | 2-CH₃, 5-NO₂ | —CH₂CH₂N(CH₂CH₃)₂ | —CH₃ | O |
| 107 | 2-N(CH₃)₂, 5-NO₂ | —CH₂CHN(CH₃)₂<br>           \|<br>          CH₃ | —CH₂CH₂CH₃ | O |
| 108 | 2-NH₂ | —CH₂CH₂N(CH₃)₂ | —C₆H₅ | O |
| 109 | 2-CH₃, 5-NH₂ | —CH₂CH₂N(CH₂CH₃)₂ | —CH₃ | O |
| 110 | 2-N(CH₃)₂, 5-NH₂ | —CH₂CHN(CH₃)₂<br>           \|<br>          CH₃ | —CH₂CH₂CH₃ | O |

EXAMPLES 111–132

Compounds of the general formula

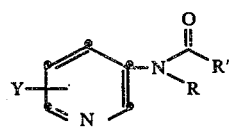

(Examples 111–130), are prepared by the following sequence of reactions: 3-aminopyridines of the general formula

where Y is listed in column A, Table II, are reacted with acetic anhydride by following the procedure of Example 47, Part B. The resulting acetamides are then alkylated with the reagents RCl where R is listed in column B according to the procedure of Example 13, Part A, and hydrolyzed according to the procedure of Example 15, Part B, to give compounds of the general formula

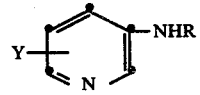

wherein Y and R are listed in columns A and B, respectively. These compounds are reacted with carbamoyl chlorides

where R' is listed in column C by following the procedure of Example 1, Part C, except Examples 111–114, which are obtained by following the procedure of Example 60, Part D, to give the corresponding pyridylureas of the general formula

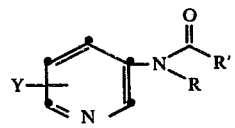

where Y, R and R' have the same meaning as in columns A, B and C, respectively, of Table II.

In addition the nitro-substituted pyridylureas (Examples 129 and 130) are reduced to give the corresponding amino-substituted pyridylureas (Examples 131 and 132) by following the procedure of Example 71, Part C.

TABLE II

| EXAMPLE | A<br>Y | B<br>R | C<br>R' |
|---|---|---|---|
| 111 | 2-CH$_3$ | —CH$_2$CH$_2$[CH(CH$_3$)$_2$]$_2$ | —N(CH$_3$)$_2$ |
| 112 | 4-CH$_3$ | —CH$_2$CH$_2$[CH(CH$_3$)$_2$]$_2$ | —N(CH$_2$CH$_3$)$_2$ |
| 113 | 4-CH$_2$CH$_3$ | —CH$_2$CH$_2$[CH(CH$_3$)$_2$]$_2$ | —N(CH$_3$)(C$_6$H$_5$) |
| 114 | 6-CH$_2$CH$_3$ | —CH$_2$CH$_2$[CH(CH$_3$)$_2$]$_2$ | —N(piperidine) |
| 115 | 6-C$_6$H$_5$ | —CH$_2$CH$_2$N(CH$_3$)$_2$ | —N(CH$_3$)$_2$ |
| 116 | 2-OCH$_3$ | —CH$_2$CH$_2$N(CH$_2$CH$_3$)$_2$ | —N(CH$_3$)(C$_6$H$_5$) |
| 117 | 6-OCH$_3$ | —CH$_2$CH$_2$N(pyrrolidine) | —N(piperazine)NCH$_2$C$_6$H$_5$ |
| 118 | 2-SCH$_3$ | —CH$_2$CH$_2$CH$_2$N(CH$_3$)$_2$ | —N(CH$_3$)$_2$ |
| 119 | 2-N(CH$_3$)$_2$ | —CH$_2$CH$_2$CH$_2$N(CH$_2$CH$_2$CH$_3$)$_2$ | —N(CH$_3$)$_2$ |
| 120 | 4-N(CH$_3$)$_2$ | —CH$_2$CH$_2$N(CH$_2$CH$_2$CH$_3$)$_2$ | —N(CH$_2$CH$_3$)$_2$ |
| 121 | 6-N(morpholine) | —CH$_2$CH(CH$_3$)N(CH$_3$)$_2$ | —N(pyrrolidine) |
| 122 | 6-F | —CH$_2$C(CH$_3$)$_2$N(CH$_3$)$_2$ | —N(CH$_3$)$_2$ |
| 123 | 6-Cl | —CH$_2$CH$_2$N(piperidine) | —N(CH$_3$)(C$_6$H$_5$) |
| 124 | 4-SO$_2$CH$_3$ | —CH$_2$CH$_2$N(morpholine) | —N(CH$_2$CH$_3$)$_2$ |
| 125 | 2-CH$_3$, 6-OCH$_3$ | —CH$_2$CH$_2$N(CH$_2$CH$_3$)$_2$ | —N(pyrrolidine) |
| 126 | 2,6-diOCH$_3$ | —CH$_2$CH$_2$N(CH$_3$)$_2$ | —N(piperidine) |
| 127 | 2-Cl, 6-OCH$_3$ | —CH$_2$CH$_2$N(CH$_3$)CH(CH$_3$)$_2$ | —N(piperazine)NCH$_2$C$_6$H$_5$ |
| 128 | 2,6-diCl | —CH$_2$CH$_2$N(CH$_2$CH$_3$)$_2$ | —N(CH$_3$)$_2$ |
| 129 | 5-NO$_2$ | —CH$_2$CH$_2$N(CH$_2$C$_6$H$_5$)$_2$ | —N(CH$_2$CH$_3$)$_2$ |
| 130 | 6-NO$_2$ | —CH$_2$CH$_2$N—(cyclohexyl)$_2$ | —N(CH$_3$)(C$_6$H$_5$) |
| 131 | 5-NH$_2$ | —CH$_2$CH$_2$N(CH$_2$C$_6$H$_5$)$_2$ | —N(CH$_2$CH$_3$)$_2$ |
| 132 | 6-NH$_2$ | —CH$_2$CH$_2$N—(cyclohexyl)$_2$ | —N(CH$_3$)(C$_6$H$_5$) |

EXAMPLE 133

N,N-Dimethyl-N'-(2-dimethylaminoethyl)-N'-(2-chloro-4-pyridyl)urea Dihydrochloride A. 4-(2-Dimethylaminoethylamino)-2-chloropyridine The title compound is obtained by following the procedure of Example 38, Part A, except substituting 2-chloro-4-nitropyridine for 2,6-dichloropyridine and omitting the solvent pyridine.

B.

N,N-Dimethyl-N'-(2-dimethylaminoethyl)-N'-(2-chloro-4-pyridyl)urea Dihydrochloride The title compound is obtained by following the procedure of Example 12 except substituting 4-(2-dimethylaminoethylamino)-2-chloropyridine from Part A above for 2-(2-dimethylaminoethylamino)-4-methylpyridine. The product melts at 181°–186°.

EXAMPLE 134

N,N-Dimethyl-N'-(2-dimethylaminoethyl)-N'-(4-pyridyl)urea

A. N-(2-Dimethylaminoethyl)-N-(4-pyridyl)acetamide

The title compound is obtained by following the procedure of Example 13, Part A, except substituting N-(4-pyridyl)acetamide for N-(5-methyl-2-pyridyl)acetamide.

B. 4-(2-Dimethylaminoethylamino)pyridine

The title compound is prepared by following the procedure of Example 15, Part B, except substituting N-(2-dimethylaminoethyl)-N-(4-pyridyl)acetamide from Part A above for N-(2-dimethylaminoethyl)-N-(5-chloro-2-pyridyl)acetamide. The product has b.p. 120°–128°/0.7 mm.

C. N,N-Dimethyl-N'-(2-dimethylaminoethyl)-N'-(4-pyridyl)urea

The title compound is prepared by following the procedure of Example 12 except substituting 4-(2-dimethylaminoethylamino)pyridine for 2-(2-dimethylaminoethylamino)-4-methylpyridine.

EXAMPLES 135–150

Compounds of the general formula

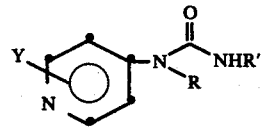

(Examples 135–148), are prepared by the following sequence of reactions: 4-aminopyridines of the general formula

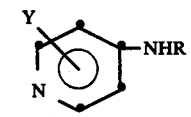

where Y is listed in colum A, Table III are reacted with acetic anhydride by following the procedure of Example 47, Part B. The resulting acetamides are then alkylated with the reagents RCl where R is listed in column B according to the procedure of Example 13, Part A, and hydrolyzed according to the procedure of Example 15, Part B, to give compounds of the general formula

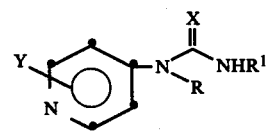

wherein Y and R have the same meaning as in columns A and B, respectively. These compounds are reacted with an isocyanate or isothiocyanate, $R'N=C=X$, wherein $R'$ and X are listed in column C by following the procedure of Example 1, Part C, to give the corresponding pyridylureas of the general formula where Y, R, $R^1$ and X have the same meaning as in columns A, B and C, respectively of Table III.

In addition the nitro-substituted pyridylureas (Examples 147 and 148) are reduced to give the corresponding amino-substituted pyridylureas (Examples 149 and 150) by following the procedure of Example 71, Part C.

TABLE III

| EXAMPLE | A<br>Y | B<br>R | C<br>R' | X |
|---|---|---|---|---|
| 135 | 2-$CH_3$ | —$CH_2CH_2N(CH_3)_2$ | —$CH_3$ | O |
| 136 | 3-$CH_3$ | —$CH_2CH_2NCH(CH_3)_2$<br>\|<br>$CH_3$ | —$CH_2CH_2CH_3$ | O |
| 137 | 2-$C_6H_5$ | —$CH_2CH_2N(CH_2CH_5)_2$ | cyclohexyl | O |
| 138 | 3-$OCH_3$ | —$CH_2CH_2CH_2N(CH_3)_2$ | —$C_6H_5$ | O |
| 139 | 2-$N(CH_3)_2$ | —$CH_2CHN(CH_3)_2$<br>\|<br>$CH_3$ | —$CH_3$ | S |
| 140 | 3-$N(CH_3)_2$ | —$CH_2CH_2N$⌒O⌒ (morpholino) | —$CH(CH_3)_2$ | O |
| 141 | 3-Cl | —$CH_2CH_2N$(dicyclohexyl)$_2$ | —$CH_2(CH_2)_2CH_3$ | O |
| 142 | 2-F | —$CH_2CH_2N(CH_2CH_2CH_3)_2$ | —$CH_3$ | O |
| 143 | 2,6-diCl | —$CH_2CH_2NCH(CH_3)_2$<br>\|<br>$CH_3$ | —$CH_3$ | S |

TABLE III-continued

| | A | B | C | |
|---------|---|---|----|---|
| EXAMPLE | Y | R | R' | X |
| 144 | 2,5-diCl | —CH₂C(CH₃)₂N(CH₃)₂ | —CH(CH₃)₂ | O |
| 145 | 2-CF₃; 3,5-diCl | —CH₂CH₂N⟨ring⟩ | —CH₂CH₂CH₃ | O |
| 146 | 2-SO₂CH₃; 3,5-diCl | —CH₂CH₂N(CH₂C₆H₅)₂ | —CH₃ | S |
| 147 | 2-Cl, 5-NO₂ | —CH₂CH₂N(CH₂CH₃)₂ | —CH₃ | O |
| 148 | 2-Cl, 5-NO₂, 6-OCH₂CH₃ | —CH₂CH₂N(CH₃)₂ | —CH₂CH₂CH₃ | O |
| 149 | 2-Cl, 5-NH₂ | —CH₂CH₂N(CH₂CH₃)₂ | —CH₃ | O |
| 150 | 2-Cl, 5-NH₂, 6-OCH₂CH₃ | —CH₂CH₂N(CH₃)₂ | —CH₂CH₂CH₃ | O |

EXAMPLES 151–164

Compounds of the general formula

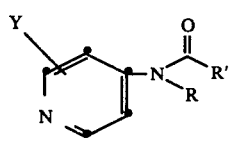

(Examples 151–162) are prepared by the following sequence of reactions: 4-aminopyridines of the general formula

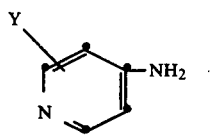

where Y is listed in column A, Table IV, are reacted with acetic anhydride by following the procedure of Example 47, Part B. These resulting acetamides are then alkylated with the reagents RCl, where R is listed in column B, according to the procedure of Example 13, Part A, and hydrolyzed according to the procedure of Example 15, Part B, to give compounds of the general formula

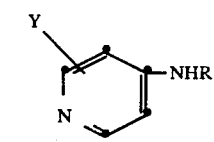

where Y and R are listed in columns A and B, respectively. These compounds are reacted with carbamoyl chlorides $$\underset{\underset{\text{R'CCl,}}{\|}}{O}$$

where R' is listed in column C, by following the procedure of Example 1, Part C, except Examples 151–153 which are obtained by following the procedure of Example 60, Part D, to give the corresponding pyridylureas of the general formula

where Y, R and R' have the same meaning as in columns A, B and C, respectively of Table IV.

In addition, the nitro-substituted pyridylureas (Examples 161 and 162) are reduced to give the corresponding amino-substituted pyridylureas (Examples 163 and 164) by following the procedure of Example 71, Part C.

TABLE IV

| | A | B | C |
|---------|---|---|----|
| EXAMPLE | Y | R | R' |
| 151 | 2-CH₂CH₃ | —CH₂CH₂N[CH(CH₃)₂]₃ | —N(CH₃)₂ |
| 152 | 2-C(CH₃)₃ | —CH₂CH₂N[CH(CH₃)₂]₃ | —N(CH₂CH₃)₂ |
| 153 | 2-OCH₃ | —CH₂CH₂N[CH(CH₃)₂]₃ | —N⟨piperidine⟩ |
| 154 | 2-OCH₂CH₃ | —CH₂CH₂N(CH₃)₂ | —NCH₃ \| C₆H₅ |
| 155 | 2-N⟨ring⟩ | —CH₂CH₂N(CH₂CH₃)₂ | —N(CH₃)₂ |
| 156 | 2-N⟨morpholine⟩O | —CH₂CH₂CH₂N(CH₃)₂ | —N(CH₂CH₃)₂ |

TABLE IV-continued

| EXAMPLE | A<br>Y | B<br>R | C<br>R' |
|---|---|---|---|
| 157 | 2,6-diCH$_3$ | —CH$_2$CH$_2$N(cycloheptyl ring) | —N(cycloheptyl ring) |
| 158 | 2,6-diOCH$_3$ | —CH$_2$CHN(CH$_3$)$_2$<br>     \|<br>     CH$_3$ | —N(piperazinyl)NCH$_2$C$_6$H$_5$ |
| 159 | 2-Cl, 6-CF$_3$ | —CH$_2$CH$_2$N(morpholino) | —N(CH$_3$)$_2$ |
| 160 | 2,6-diCH$_3$, 3-Cl | —CH$_2$CH$_2$N(CH$_2$CH$_2$CH$_3$)$_2$ | —NCH$_3$<br>  \|<br>  C$_6$H$_5$ |
| 161 | 3-NO$_2$ | —CH$_2$CH$_2$N(CH$_3$)$_2$ | —N(piperidinyl) |
| 162 | 2-NO$_2$ | —CH$_2$CH$_2$N—(cyclohexyl)$_2$ | —N(CH$_3$)$_2$ |
| 163 | 3-NH$_2$ | —CH$_2$CH$_2$N(CH$_3$)$_2$ | —N(pyrrolidinyl) |
| 164 | 2-NH$_2$ | —CH$_2$CH$_2$N—(cyclohexyl)$_2$ | —N(CH$_3$)$_2$ |

EXAMPLE 165

N,N-Dimethyl-N'-(2-diisopropylaminoethyl)-N'-(4-methoxy-2-pyridyl)urea

A.
2-(2-Diisopropylaminoethylamino)-4-nitropyridine-N-oxide

A mixture of 2-chloro-4-nitropyridine-N-oxide (20.9 g., 0.12 mole) and 2-diisopropylaminoethylamine (34.8 g., 0.24 mole) dissolved in absolute ethanol (200 ml) is refluxed for 3½ hours. The solvent is evaporated and the residue is extracted with hot cyclohexane several times to give upon cooling orange crystalline product (20.9 g.), m.p. 94°–97° C.

B.
2-(2-Diisopropylaminoethylamino)-4-methoxypyridine-N-oxide 2-(2-Diisopropylaminoethylamino)-4-nitropyridine-N-oxide (10.0 g., 35.5 mmole) is added to a solution of sodium methoxide (3.0 g., 55 mmole) in dry methanol (100 ml.) and refluxed for 4 hours. The solvent is evaporated and the residue dissolved in chloroform, washed with water, dried over sodium sulfate and evaporated to give oily product.

C.
2-(2-Diisopropylaminoethylamino)-4-methoxypyridine 2-(2-diisopropylaminoethylamino)-4-methoxypyridine-N-oxide (4.3 g., 15 mmole) dissolved in glacial acetic acid (32 ml.) is refluxed with iron powder (8.2 g.) for three hours. The reaction mixture is filtered to remove insoluble salts and then the solvent evaporated. The residue is dissolved in methanol, treated with excess potassium hydroxide pellets and filtered to remove more insoluble salts. The concentrate solution is dissolved in chloroform, washed with water, dried over sodium sulfate, filtered through a pad of charcoal and evaporated to give oily product.

D.
N,N-Dimethyl-N'-(2-diisopropylaminoethyl)-N'-(4-methoxy-2-pyridyl)urea

The title compound is obtained by following the procedure of Example 60, Part D except substituting 2-(2-diisopropylaminoethylamino-4-methoxypyridine from Part C for 2-(2-dimethylaminoethylamino)-3, dichloropyridine. The product boils at 168°–170°, 0.7 mmole.

EXAMPLE 166

N,N-Dimethyl-N'-(2-diisopropylaminoethyl)-N'-(4-methylthio-2-pyridyl)urea

The title compound is obtained by following the procedure of Example 165 except in Part C substituting sodium methyl mercaptide for sodium methoxide. The product boils at 176°–178°/0.5 mm.

EXAMPLE 167

N,N-bis(2-hydroxyethyl)-N'-(2-diisopropylaminoethyl)-N'-(4,6-dimethyl-2-pyridyl(urea Hydrochloride A. N,N-bis(benzyloxyethyl)benzylamine Diethanolamine (42.0 g., 0.4 mole) is stirred under nitrogen in 800 ml. of dry DMF at 0° C. and 50% NaH in mineral oil (57.6 g., 1.2 mole) is added in small portions. After the sodium hydride has reacted, benzyl bromide (205.3 g., 1.2 mole) is added dropwise. The mixture is allowed to come to room temperature while stirring overnight. The reaction mixture is poured into water and is extracted with ether. The ether solution is extracted with dilute HCl. The acid extract is basified with NaOH and extracted with ether. Crude product is recovered by drying, filtering and evaporating the ether. The residual liquid (138.4 g.) is subjected to distillation at 290° C. and 0.01 mm. to remove volatile impurities. This gives 114.4 g. of amber oil.

N,N-bis(benzyloxyethyl)carbamoylchloride

A 12.5% solution of phosgene in benzene (87.1 g., 0.11 mole) is cooled to 5° C. and stirred as N,N-bis(benzyloxyethyl)benzylamine (37.6 g., mole) is added dropwise. The resulting solution is stirred at room temperature under nitrogen overnight. Then the solution is evacuated at 40°–45° C. and 0.2 mm. to remove the solvent and benzyl chloride. The residual liquid (37.0 g.) is sufficiently pure for synthetic purposes.

C.
N,N-bis(2-benzyloxyethyl)-N'-(2-diisopropylaminoethyl)-N'-(4,6-dimethyl-2-pyridyl)urea The title compound is obtained following the procedure of Example 29 except substituting 2-(2-diisopropylamonoethylamino-4,6-dimethylpyridine for 2-(2-dimethylaminoethylamino)-4,6-dimethylpyridine, bis(2-benzyloxyethyl)carbamoyl chloride for dimethyl carbamoyl chloride, and dry xylene for the solvent toluene.

D.
N,N-bis(2-hydroxyethyl)-N'-(2-diisopropylaminoethyl)-N'-(4,6-dimethyl-2-pyridyl)urea Hydrochloride The title compound is obtained following the procedure of Example 41, Part C, except substituting N,N-bis(2-benzyloxyethyl)-N'-(2-diisopropylaminoethyl)-N'-(4,6-dimethyl-2-pyridyl)urea for N,N-dimethyl-N'-2-[N-(2-benzyloxyethyl)-N-methyl -N'-(4,6-dimethyl-2-pyridyl)urea.

EXAMPLE 168

N,N-Dimethyl-N'-(2-diisopropylaminoethyl)-N'-(6-methyl-2-pyridyl)urea Hydrochloride A.
2-(2-Diisopropylaminoethylamino)-6-methylpyridine The title compound is obtained by following the procedure of Example 1, Part A, except substituting N-(6-methyl-2-pyridyl)acetamide for N-(4,6-dimethyl-2-pyridyl)acetamide and 2-diisopropylaminoethyl chloride hydrochloride for 2-dimethylaminoethyl chloride hydrochloride and submitting this product directly to the procedure of Example 15, Part B. The product boils at 125°–128°/0.7 mm.

B.
N,N-Dimethyl-N'-(2-diisopropylaminoethyl)-N'-(6-methyl-2-pyridyl)urea Hydrochloride The title compound is obtained by following the procedure of Example 29 except substituting 2-(2-diisopropylaminoethylamino)-6-methylpyridine for 2-(2-dimethylaminoethylamino)-4,6-dimethylpyridine, dimethyl carbamoyl chloride for diethyl carbamoyl chloride and substituting ethanolic hydrogen chloride for hydrogen bromide. The product melts at 156.5°–157.5°.

EXAMPLE 169

N,N-Dimethyl-N'-(2-diisopropylaminoethyl)-N'-(6-difluoromethyl-4-methyl-2-pyridyl)urea Hydrochloride A.
N,N,-Dimethyl-N'-(2-diisopropylaminoethyl)-N'-(6-formyl-4-methyl-2 -pyridyl)urea and its Hydrochloride N'-(6-hydroxymethyl-4-methyl-2-pyridyl)-N,N-dimethyl-N'-(2-diisopropylaminoethyl)urea (6.73 g., 0.02 mole) is refluxed under nitrogen in 100 ml. of chloroform with 30 g. of activated MnO$_2$ for 48 hours. Filtration of the hot reaction mixture and concentration in vacuo gives 6.2 of red oil. (Conversion of a 2.0 g. sample to the hydrochloride salt with ethanolic-HCl gives 1.0 g. of white solid after recrystallization from ethanol-ether, m.p. 142°–148° C.

B.
N,N-Dimethyl-N'-(2-diisopropylaminoethyl)-N'-(6-difluoromethyl-4-methyl-2-pyridyl)urea Hydrochloride The N'-(6-formyl-4-methyl-2-pyridyl)-N,N-dimethyl-N'-(2-diisopropylaminoethyl)urea (6.7 g., 0.02 mole) is refluxed in 50 ml. of benzene with diethylaminosulfurtrifluoride (DAST) (6.7 g., 0.042 mole) for 5 hours. The dark mixture is poured into ice cold NaHCO$_3$, extracted with ether, dried and concentrated in vacuo. The amber liquid obtained (3.4 g.) is converted to the hydrochloride salt with ethanolic HCl. Recrystallization from ethanol-ether gives 1.7 g. m.p. 154°14 162° C.

EXAMPLE 170

N,N-Dimethyl=N'-(2-diisopropylaminoethyl)-N'-(4-trifluoromethyl-2-pyridyl)urea

A.
2-(2-Diisopropylaminoethylamino)-4-trifluoromethyl-6-chloropyride

The title compound is obtained by following the procedure of Example 38, Part A, except substituting 4-trifluoromethyl-2,6-dichloropyridine for 2,6-dichloropyridine and N,N-diisopropylethylene diamine for N,N-dimethylene diamine.

B.
2-(2-Diisopropylaminoethylamino)-4-trifluoromethylpyridine

The title compound is obtained by following the procedure of Example 55, Part A, except substituting 2-(2-diisopropylaminoethylamino)-4-trifluoromethyl-6-chloropyridine from Part A for 2-(2-dimethylaminoethylamine)-4-trifluoromethyl-6-chloropyridine.

C.
N,N-Dimethyl-N'-(2-diisopropylaminoethylamino)-N'-(4-trifluoromethyl-2-pyridyl)urea The title compound is obtained by following the procedure of Example 60, Part D, except substituting 2-(2-diisopropylaminoethylamino)-4-trifluoromethyl-6-chloropyridine from Part B above for 2-(2-dimethylaminoethylamino)-3,5-dichloropyridine and lithium 2,2,6,6-tetramethylpiperidide for n-butyl lithium and omitting the treatment with ethanolic hydrogen chloride. The product boils at 140°–143°/0.25 mm.

EXAMPLE 171
N,N-Dimethyl-N'-(2-diisopropylaminoethyl)-N'-(4-trifluoromethyl-6-methylamino-2-pyridyl)urea

A.
2-(2-Diisopropylaminoethylamine)-4-trifluoromethyl-6-methylbenzylaminopyridine The title compound is obtained by following the procedure of Example 54, Part A, except substituting 2-(2-diisopropylaminoethylamino)-4-trifluoromethyl-6-chloropyridine for 2-(2-dimethylaminoethylamino)-4-trifluoromethyl-6-chloropyridine for 2-(2-dimethylaminoethylamino)-4-trifluoromethyl-6-chloropyridine.

B.
N,N-Dimethyl-N'-(2-diisopropylaminoethyl)-N'-(4-trifluoromethyl-6-methylbenzylamino-2-pyridyl)urea The title compound is obtained by following the procedure of Example 60, Part D, except substituting 2-(2-diisopropylaminoethylamine)-4-trifluoromethyl-6-methylbenzylaminopyridine for 2-(2-dimethylaminoethylamino)-3,5-chloropyridine and lithium 2,2,6,6-tetramethylpiperidide for butyl lithium and omitting the ethanolic hydrogen chloride treatment.

C.
N,N-Dimethyl-N'-(2-diisopropylaminoethyl)-N'-(4-trifluoromethyl-6-methylamino-2-pyridyl)urea The title compound is obtained by following the procedure of Example 54, Part C, except substituting N,N-dimethyl-N'-(2-diisopropylaminoethyl)-N'-(4-trifluoromethyl-6-methylbenzylamino-2-pyridyl)urea for N,N-dimethyl-N'-(2-dimethylaminoethyl)-N'-(4-trifluoromethyl-6-methylbenzylamino-2-pyridyl)urea. The product melts at 92°–94°.

EXAMPLE 172
N,N-Dimethyl-N'-(2-diisopropylaminoethyl)-N'-4,6-bis(trideuteromethyl)-2-pyridyl)urea Hydrochloride A solution of N,N-dimethyl-N'-(2-diisopropylaminoethyl)-N'-(4,6-dimethyl-2-pyridyl)urea (10.6 g., 33 mmole) in perdeuterodimethyl sulfoxide containing potassium t-butoxide (100 mg.) is heated at 90° for 21 hours. Dilute reaction mixture with methylene chloride, wash with water, dry over sodium sulfate, filtered thru a charcoal pad and evaporated. Dissolve residue in isopropanol, treat with one equivalent of ethanolic hydrogen chloride, dilute with diethyl ether and collcet product (10.8 g.), m.p. 189°–191°.

EXAMPLE 173
N,N-Dimetyl-N'-(6-diisopropylaminohexyl)-N'-(5-methyl-3-pyridyl)urea

A.
3-(6-Diisopropylaminohexylamino)-5-methylpyridine

The title compound is obtained by following the procedure of Example 1, Part A, except substituting N-(5-methyl-3-pyridyl) acetamide for N-(6-dimethyl-2-pyridyl)acetamide, 6-diisopropylaminohexyl bromide for dimethylaminoethyl chloride hydrochloride and submitting this product directly to the procedure of Example 15, Part B. The product boils at 190°–195°/1.2 mm.

B.
N,N-Dimethyl-N'-(6-diisopropylaminohexyl)-N'-(5-methyl-3-pyridyl)urea Dihydrobromide The title compound is obtained by following the procedure of Example 29 except substituting 3-(6-diisopropylaminohexylamino)-5-methylpyridine for 2-(2-dimethylaminoethylamino)-4,6-dimethylpyridine and dimethyl carbamoyl chloride for diethyl carbamoyl chloride. The product melts at 190°–192°.

EXAMPLE 174
N,N-Dimethyl-N'-(2-diisopropylaminoethyl)-N'-(4-methyl-6-hydroxymethyl-2-pyridyl)urea Hydrochloride and
N,N-Dimethyl-N'-(2-diisopropylaminoethyl)-N'-(4-hydroxymethyl-6-methyl-2-pyridyl)urea Hydrochloride

A. Ethyl 3-Imino-3-(2-diisopropylaminoethylamino)propionate

To a solution of N,N-dissopropyl-1,2-ethanediamine (14.4 g., 0.1 mole) in absolute ethanol (40 ml.) under anhydrous conditions is added in one portion ethyl etoxycarbonylacetimidate hydrochloride (200 g., 0.1 mole). The solution is stirred at ambient temperature for 12–24 hours and then the solvent removed under vacuum. The product slowly crystallizes in nearly quantitative yield, m.p. 64°–67°.

B.
2-(Diisopropylaminoethylamino)-4-benzyloxymethyl-3-ethoxycarbonyl-6-methylpyridine and
2-(diisopropylaminoethylamino)-6-benzyloxymethyl-3-ethoxycarbonyl-4-methylpyridine A solution of 1-benzyloxy-2,4-pentamidione (6.18 g., 0.03 mole) and ethyl 3-imino-(2-diisopropylaminoethylamino)propionate (7.71 g., 0.03 mole) in 60 ml. of dry benzene is heated at reflux for 18 hours. Anhydrous $Na_2SO_4$ is added to the reaction mixture at RT. The mixture is filtered and evaporated in vacuo. This gives 12.4 g. of amber oil which is an isomeric mixture of the title compounds (ratio 4:1).

C.
2-(Diisopropylaminoethylamino)-4-benzyloxymethyl-3-carboxy-6-methylpyridine and
2-(diisopropylaminoethylamino)-benzyloxymethyl)-3-carboxy-4-methylpyridine To a solution of the isomeric mixture of the pyridyl ester (103.7 g., 0.235 mole) in 500 ml. of ethanol is added 85% potassium hydroxide (31.0 g., 0.47 mole). The solution is stirred at reflux for 16 hours. The reaction is cooled in ice and neutralized with 6 N ethanolic HCl (78 ml., 0.47 mole), filtered and concentrated in vacuo. This gives 94 g. of oil which is a mixture of the pyridylcarboxylic acids.

D. 2-(Diisopropylaminoethylamino)-4-benzyloxymethyl-6-methylpyridine and 2-Diisopropylaminoethylamino)-6-benzyloxymethyl-4-methylpyridine The isomeric mixture of pyridylcarboxylic acids (94 g., 0.235 mole) is dissolved in 200 ml. of m-dimethoxybenzene and copper powder (10 g.) is added. The mixture is stirred at 210°–215° C. for 3 hours under $N_2$. The cooled mixture is diluted with 200 ml. of ether and is filtered. The filtrate is extracted with 3NHCl. The acidic extract is basified with sodium carbonate and is extracted with ether. The ether solution is filtered through activated carbon, dried and concentrated in vacuo. This procedure gives 51.2 g. of the title compounds as an isomeric mixture.

E. N,N-Dimethyl-N'-(2-diisopropylaminoethyl)-N'-(4-methyl-6-benzyloxymethyl-2-pyridyl)urea and N,N-dimethyl-N'-(2-diisopropylaminoethyl)-N'-(4-benzyloxy-6-methyl-2-pyridyl)urea The title compounds are obtained as a mixture by following the procedure of Example 60, Part D, except substituting the mixture from Part D above for 2-(2-dimethylaminoethylamino)-3,5-dichloropyridine.

F. N,N-Dimethyl-N'-(2-diisopropylaminoethyl)-N'-(4-methyl-6-hydroxymethyl-2-pyridyl)urea Hydrochloride and N,N-dimethyl-N'-(2-diisopropylaminoethyl)-N'-(4-hydroxymethyl-6-methyl-2-pyridyl)urea Hydrochloride The title compounds are obtained by following the procedure of Example 74, except substituting the mixture from Part E above for N,N-dimethyl-N'-(2-dimethylaminoethyl)-N'-(6benzyloxy-2-pyridyl)urea. The resulting mixture is chromatographed on a silica gel column using chloroform saturated with ammonium hydroxide. The separated compounds are treated with ethanolic hydrogen chloride to give N,N-dimethyl-N'-(2-diisopropylaminoethyl)-N'-(4-methyl-6-hydroxymethyl-2-pyridyl)urea hydrochloride, m.p. 168°–170°, and N,N-dimethyl-N'-(2-diisopropylaminoethyl)-N'-(4-hydroxymethyl-6-methyl-2-pyridyl)urea hydrochloride, m.p. 210°–212°.

EXAMPLE 175

N,N-Dimethyl-N'-(N"-cyclopropyl-N"-isopropylaminoethyl)-N'-(4,6-dimethyl-2-pyridyl)urea

A. 2-(2,2-Diethoxyethylamino)-4,6-dimethylpyridine 4,6-Dimethyl-2-pyridylamine (24.4 g., 0.2 mole) is stirred in 250 ml. of dry xylene under nitrogen atmosphere and 50% NaH in mineral oil (8.6 g., 0.2 mole) is added. The mixture is heated at 130° C. for 1 hour. Then it is cooled slightly and diethyl bromoacetal (47.5 g., (0.24 mole) is added. The suspension is heated at reflux for 16 hours after which it is cooled and filtered. The solvent is removed in vacuo and the residual liquid is distilled. Product is collected at 117°–126° C. at 0.7 mm. wt. is 27.3 g.

B. N,N-Dimethyl-N'-(2,2-diethoxyethyl)-N'-(4,6-dimethyl-2-pyridyl)urea

The title compound is obtained by following the procedure of Example 29 except substituting 2-(2,2-diethoxyethylamino)-4,6-dimethylpyridine for 2-(2-dimethylaminoethylamino)-4,6-dimethylpyridine and omitting the treatment with hydrogen bromide. The product boils at 145°–149°/0.4 mm.

C. N,N-Dimethyl-N-(formylmethyl)-N'-(4,6-dimethyl-2-pyridyl)urea

N,N-Dimethyl-N'-(2,2-diethoxyethyl)-N'-(4,6-dimethyl-2-pyridyl)urea (9.28 g., 0.03 mole) is stirred in 80 ml. of 1.5 NHCl at room temperature for 2 to 3 hours. The reaction is basified with $Na_2CO_3$ and extracted with ether. The ether solution is dried, filtered and concentrated in vacuo. This gives 5.5 g. of the aldehyde as an amber oil.

D. N,N-Dimethyl-N'-(N"'-cyclopropyl-N"-isopropylaminoethyl-N'-(4,6-dimethyl-2-pyridyl)urea N,N-dimethyl-N'-(formylmethyl)-N-(4,6-dimethyl-2-pyridyl)urea (4.45 g., 18.9 mmoles) and N-cyclopropyl-N-isopropylamine (5.63 g., 56.7 mmoles) are dissolved in methanol (15 ml.) and cooled in an ice bath. To this cooled solution is added 1.9 ml. (10 mmoles) of 5.2 N ethanolic HCl followed by the addition of sodium cyanoborohydride (1.13 g., 11.35 mmoles). The reaction is stirred at ambient temperature for 9 days, and the solvent removed to leave 5.45 g. of crude product. The product is further purified by distillation under reduced pressure and boils at 143°–145°/0.025 mm.

Following the procedure of Example 175 the following compounds are prepared:

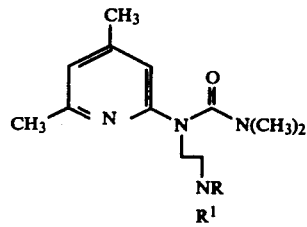

| Example No. | R | R¹ | Salt | m.p. (b.p.) |
|---|---|---|---|---|
| 176 | H | ▷ | HCl | 138°–139.5° |
| 177 | CH₃ | ▷ | — | (122°–125°/0.02 mm) |
| 178 | CH₂–▷ | ▷ | — | (154°–157°/0.2 mm) |
| 179 | CH₂–▷ | CH₂–▷ | — | (160°–165°/0.15 mm) |

EXAMPLE 180

N,N-Dimethyl-N'-(8-diisopropylaminooctyl)-N'-(5-methyl-3-pyridyl)urea Dihydrobromide

A.

3-(8-Diisopropylaminooctylamino)-5-methylpyridine

The title compound is obtained by following the procedure of Example 1, Part A, except substituting N-(5-methyl-3-pyridyl)acetamide for N-(4,6-dimethyl-2-pyridyl)acetamide, 8-diisopropylaminooctyl bromide for dimethylaminoethyl chloride hydrochloride and submitting this product directly to the procedure of Example 15, Part B. The product melts at 59°–61°.

B.

N,N-Dimethyl-N'-(8-diisopropylaminooctyl)-N-'-(5-methyl-3-pyridyl)urea Dihydrobromide The title compound is obtained by following the procedure of Example 29 except substituting 3-(8-diisopropylaminooctylamino)-5-methylpyridine for 2-(2-dimethylaminoethylamino)-4,6-dimethylpyridine and dimethyl carbamoyl chloride for diethylcarbamoyl chloride and omitting the treatment with hydrogen bromide. The product boils at 203°/0.2 mm.

EXAMPLE 181

PREPARATION OF CAPSULE FORMULATION

| Ingredient | Milligrams per Capsule |
|---|---|
| N-2-(Dimethylaminoethyl)-N-(4,6-dimethyl-2-pyridyl)-N'-hexylurea Hydrochloride | 40 |
| Starch | 440 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 182

PREPARATION OF TABLET FORMULATION

| Ingredient | Milligrams per Tablet |
|---|---|
| N-(2-Diisopropylaminoethyl)-N-(4,6-dimethyl-2-pyridyl)-N,N'-dimethyl-urea dihydrochloride | 20 |
| Lactose | 200 |
| Corn starch (for mix) | 50 |
| Corn starch (for paste) | 50 |
| Magnesium stearate | 6 |

The active ingredient, lactose and corn starch (for mix), are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 20 milligrams of active ingredient.

EXAMPLE 183

PREPARATION OF ORAL SYRUP FORMULATION

| Ingredient | Amount |
|---|---|
| N,N-dimethyl-N'-(2-dimethylaminomethyl)-N'-(6-amino-2-pyridyl)urea | 50 mg. |
| Sorbitol solution (70% N.F.) | 40 ml. |
| Sodium benzoate | 150 mg. |
| Sucaryl | 90 mg. |
| Saccharin | 10 mg. |
| Cherry Flavor | 50 mg. |
| Distilled water qs to | 100 ml. |

The sorbitol solution is added to 40 milliliters of distilled water and the active ingredient is suspended therein. The sucaryl, saccharin, sodium benzoate, and flavor are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors may be used in place of those listed above.

What is claimed is:

1. A compound of the formula

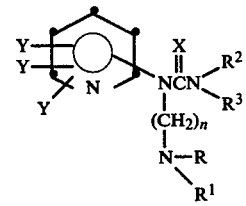

wherein n is a whole number from 2 to 8 and up to 4 hydrogen atoms in the alkylene chain $(CH_2)_n$ may be replaced by alkyl of from 1 to 3 carbon atoms;

$R, R^1, R^2$ and $R^3$ are hydrogen or alkyl of from 1 to 8 carbon atoms, aralkyl wherein alkyl is 1 to 3 carbon atoms, cycloalkyl or from 3 to 7 carbon atoms in the ring, cycloalkylmethyl with from 3 to 7 carbon atoms in the ring, alkoxyalkyl wherein alkoxy is 1 to 4 carbon atoms and alkyl is 1 to 4 carbon atoms, lower alkylcarbonyloxyalkyl, hydroxyalkyl of from 1 to 4 carbon atoms, haloalkyl of from 1 to 3 carbon atoms,

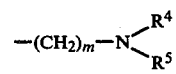

wherein m is 0, 2 or 3 and $R^4$ and $R^5$ are the same or different and are hydrogen or alkyl of from 1 to 4 carbon atoms; phenyl, substituted phenyl wherein the substituent is alkyl of from 1 to 3 carbon atoms, alkoxy of from 1 to 3 carbon atoms, halogen or haloalkyl of from 1 to 3 carbon atoms;

the Y substituents are the same or different and are hydrogen, alkyl of from 1 to 4 carbon atoms, hydroxyalkyl of from 1 to 4 carbon atoms, deuteroalkyl of from 1 to 4 carbon atoms, phenyl, hydroxy, halogen,

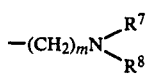

wherein m is 0–3 and $R^7$ and $R^8$ are the same or different and are hydrogen, alkyl of from 1 to 4 carbon atoms or aralkyl wherein alkyl is 1 to 3 carbon atoms; haloalkyl of from 1 to 4 carbon atoms, alkoxy of from 1 to 4 carbon atoms, aralkoxy wherein alkoxy is 1 to 3 carbon atoms, alkylthio of from 1 to 4 carbon atoms, alkylsulfonyl of 1 to 4 carbon atoms, cyano, nitro, formyl, loweralkoxycarbonoyl wherein alkoxy is 1 to 5 carbon atoms or carbamoyl;

X is oxygen or sulfur;

and the quaternary ammonium or N-oxide derivatives thereof, and the pharmaceutically acceptable acid-addition salts thereof.

2. A compound according to claim 1 of the formula

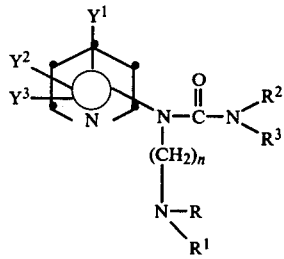

wherein n, R, $R^1$, $R^2$ and $R^3$ have the same meaning as in claim 1 and $Y^1$ is hydrogen, alkyl of from 1 to 4 carbon atoms, alkoxy of 1 to 4 carbon atoms, haloalkyl of 1 to 3 carbon atoms, hydroxyalkyl of 1 to 4 carbon atoms, deuteroalkyl of 1 to 4 carbon atoms or alkylthio of 1 to 4 carbon atoms; $Y^2$ is hydrogen, alkyl of 1 to 4 carbon atoms or halogen, and $Y^3$ is hydrogen, alkyl of from 1 to 4 carbon atoms, hydroxyalkyl of 1 to 4 carbon atoms, deuteroalkyl of 1 to 4 carbon atoms, haloalkyl of 1 to 3 carbon atoms, amino, methylamino, dimethylamino or halogen.

3. A compound according to claim 2 of the formula

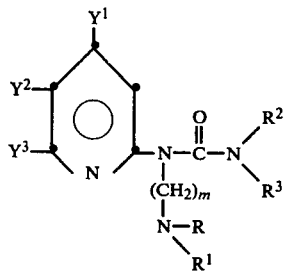

wherein $Y^1$, $Y^2$, $Y^3$, m, R, $R^1$, $R^2$ and $R^3$ have the same meaning as in claim 2.

4. A compound according to claim 3 wherein $Y^1$ is H, methyl or $CF_3$, $Y^2$ is H or chloro, and $Y^3$ is H, methyl, chloro, $CH_3$, amino, methylamino or dimethylamino.

5. A compound according to claim 3 of the formula

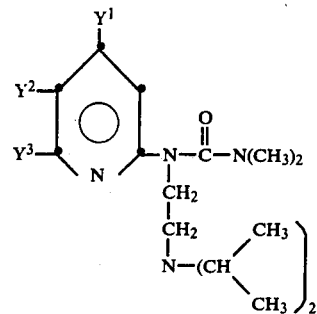

6. A compound of claim 5 wherein $Y^1$ is $CH_3$ and $Y^2$ and $Y^3$ each is H.

7. A compound of claim 5 wherein $Y^1$ and $Y^3$ each is $CH_3$ and $Y^2$ is H.

8. A compound of claim 5 wherein $Y^1$ is $CH_3$, $Y^2$ is H and $Y^3$ is Cl.

9. A compound of claim 5 wherein $Y^1$ is $CF_3$, $Y^2$ is H and $Y^3$ is $CH_3$.

10. A compound of claim 5 wherein $Y^1$ and $Y^3$ each is H and $Y^2$ is Cl.

11. A compound of claim 5 wherein $Y^1$ and $Y^3$ each is $CH_3$ and $Y^2$ is Cl.

12. A compound of claim 5 wherein $Y^1$ and $Y^2$ each is H and $Y^3$ is Cl.

13. A compound of claim 5 wherein $Y^1$ and $Y^2$ each is H and $Y^3$ is $CF_3$.

14. A compound of claim 5 wherein $Y^1$ and $Y^2$ each is H and $Y^3$ is amino.

15. A compound of claim 5 wherein $Y^1$ is $C_2H_5$ and $Y^2$ and $Y^3$ are H.

16. A compound of claim 5 wherein $Y^1$ is $-OCH_3$ and $Y^2$ and $Y^3$ are H.

17. A compound of claim 5 wherein $Y^1$ is $CF_3$ and $Y^2$ and $Y^3$ are H.

18. A compound of claim 5 wherein $Y^1$ is $CH_3$, $Y^2$ is H and $Y^3$ is $-CHF_2$.

19. A compound of claim 5 wherein $Y^1$ and $Y^2$ are H and $Y^3$ is $CH_3$.

20. A compound of claim 5 wherein $Y^1$ is $CH_3$, $Y^2$ is H and $Y^3$ is $-CH_2OH$.

21. A compound of claim 5 wherein $Y^1$ is $CH_2OH$, $Y^2$ is H and $Y^3$ is $CH_3$.

22. A compound of claim 5 wherein $Y^1$ and $Y^3$ are $-CD_3$ an $Y^2$ is H.

23. A compound of claim 5 wherein $Y^1$ is $CF_3$, $Y^2$ is H and $Y^3$ is $-NHCH_3$.

24. A compound of claim 5 wherein $Y^1$ is $-SCH_3$ and $Y^2$ and $Y^3$ are H.

25. A compound of claim 3 wherein R is cyclopropyl, $R^1$ is isopropyl, $R^2$ and $R^3$ are $CH_3$, m is 2, $Y^1$ and $Y^3$ are $CH_3$ and $Y^2$ is H.

26. A compound of claim 3 wherein R and $R^1$ are isopropyl, $R^2$ and $R^3$ are $-CH_2CH_2OH$, m is 2, $Y^1$ and $Y^3$ are $CH_3$ and $Y^2$ is H.

27. A compound of claim 2 which is N,N-dimethyl-N'-(6-diisopropylaminohexyl)-N'-(5-methyl-3-pyridyl)urea.

28. A method for inhibiting gastric acid secretion which comprises administering to a mammalian species an effective amount of a compound of claim 1.

29. A method according to claim 28 wherein the compound is administered at a dose level of from about 10 to about 200 mg.kg.

30. A composition comprising an effective amount of a compound of claim 1 in combination with a pharmaceutically acceptable carrier.

* * * * *